United States Patent
Abbott et al.

(10) Patent No.: US 6,586,628 B2
(45) Date of Patent: Jul. 1, 2003

(54) 3-METHOXYBENZYL THIOUREA DERIVATIVES AND IMPROVED LIPID COMPOSITIONS CONTAINING SAME

(75) Inventors: Thomas P. Abbott, Peoria, IL (US); Alan Wohlman, Northbrook, IL (US)

(73) Assignees: The United States of America, as represented by the Secretary of Agriculture, Washington, DC (US); The Fanning Corporation, Chicago, IL (US)

( * ) Notice: Subject to any disclaimer, the term of this patent is extended or adjusted under 35 U.S.C. 154(b) by 4 days.

(21) Appl. No.: 10/075,418

(22) Filed: Feb. 14, 2002

(65) Prior Publication Data

US 2002/0147365 A1 Oct. 10, 2002

Related U.S. Application Data

(63) Continuation-in-part of application No. 09/840,768, filed on Apr. 23, 2001.
(60) Provisional application No. 60/202,562, filed on May 10, 2000.

(51) Int. Cl.$^7$ ............................................. C07C 335/00
(52) U.S. Cl. ........................................... 564/26; 564/17
(58) Field of Search ...................................... 564/26, 17

(56) References Cited

U.S. PATENT DOCUMENTS

| | | | |
|---|---|---|---|
| 2,154,341 A | 4/1939 | Martin et al. | 37/16 |
| 2,662,096 A | 12/1953 | Huebner et al. | 260/552 |
| 3,483,296 A | 12/1969 | Martin et al. | 424/322 |
| 3,743,736 A | 7/1973 | Porter et al. | 424/267 |
| 3,852,348 A | 12/1974 | Teach | 260/553 |
| 3,949,089 A * | 4/1976 | Maxwell et al. | 424/326 |
| 3,991,008 A | 11/1976 | Temin et al. | 260/42.15 |
| 4,925,581 A | 5/1990 | Erickson et al. | 252/48.2 |
| 5,079,304 A | 1/1992 | DeMarco | 525/329.8 |
| 5,262,072 A | 11/1993 | Camenzind et al. | 252/32.7 |
| 5,434,283 A | 7/1995 | Wang et al. | 554/224 |
| 5,441,984 A | 8/1995 | Heath, Jr. et al. | 514/595 |
| 5,747,528 A | 5/1998 | Trivedi | 514/456 |
| 6,013,818 A | 1/2000 | O'Lenick, Jr. | 554/224 |
| 6,136,330 A | 10/2000 | Soliman et al. | 424/401 |
| 6,180,668 B1 | 1/2001 | O'Lenick, Jr. 514 | 514/547 |

FOREIGN PATENT DOCUMENTS

| | | |
|---|---|---|
| DD | 208 298 A | 5/1984 |
| EP | 0 466 639 B1 | 6/1991 |
| EP | 0 903 349 A2 | 3/1999 |
| EP | 1 155 677 | 11/2001 |
| WO | WO 96/28008 A | 9/1996 |
| WO | WO 01/85681 A2 | 11/2001 |

OTHER PUBLICATIONS

T.S. Chao et al. "Some Synergistic Antioxidants for Synthetic Lubricants," Symposium on Synthetic and Petroleum–Based Lubricants Presented Before the Division of Petroleum Chemistry, Inc., 27(2), 362–379, American Chemical Society, Las Vegas Meetings, Mar. 28–Apr. 2, 1982.

T.P. Abbott "Oxidative Stability System in Meadowfoam," Abstract from the 89$^{th}$ AOCS Annual Meeting & Expo, Chicago, Illinois, May 10–13 (1998).

M. Ettlinger et al. "The Mustard Oil of *Limnanthes Douglasii* Seed, m–Methoxybenzyl Isothiocyanate," Journal of the American Chemical Society 78, 9, 1952–1954 (1956).

M. Rechcigl, Jr. CRC Handbook of Naturally Occurring Food Toxicants, CRC Press, Inc. (Boca Raton, Florida), pp. 15–30 (1983).

S. Vaughn et al. "Isolation and Identification of 3–Methoxyphenyl) Acetonitrile as a Phytotoxin from Meadowfoam (*Limnanthes alba*) Seedmeal," Jouranl of Chemical Ecology, vol. 22, No. 10, 1939–1949 (1996).

T. Johns et al. "Anti–Reproductive and Other Medicinal Effects of *Tropaeolum Tuberosum*," Journal of Ethnopharmacology 5, 149–161 (1982).

T.A. Isbell et al. "Oxidative Stability Index of Vegetable Oils in Binary Mixtures with Meadowfoam Oil," Industrial Crops and Products 9, 115–123 (1999).

K. Tian et al. "Determination of Oxidative Stability of Oils and Fats," Anal. Chem. 71, 1692–1698 (1999).

S. El. Migirab et al. "Isothiocyanates, Thioureas et Thiocarbamates Isoles De Pentadip landra Brazzeana," Phytochemistry 16, 1719–1721 (1977).

W.W. Christie "Antioxidants," Bell & Bain Ltd., Glasgow, The Oily Press, Ltd. (Dundee, Scotland, 1988), pp. 133–159.

G. Kajimoto et al. "Changes in Organic Acid Formulation in Volatile Degradation Products During Oxidation of Oils Treated with Antioxidant," Fac. Nutr., Kobe Gakuin Univ., Kobe, Japan. Nippon Eiyo, Shokuryo Gakkaishi 51(4), 207–212 (1998).

K. Ziegler–Skylakakis "S–Oxygenation of Thiourea Results in the Formation of Genotoxic Products," Environ. Mol. Mutagen. 31(4), 362–373 (1998).

S.L. Mali et al. "Phytochemical Oxidation of Phenyl–3–(2–Pyridyl) Thiourea by Singlet Oxygen," Asian J. Chem. 5(4), 808–812 (1993).

(List continued on next page.)

*Primary Examiner*—Johann Richter
*Assistant Examiner*—Elvis O. Price
(74) *Attorney, Agent, or Firm*—Roberta L. Hastreiter; Lord, Bissell & Brook

(57) ABSTRACT

1-(3-methoxybenzyl)-3-substituted thiourea antioxidant compounds and improved lipids compositions which are supplemented with amounts of such antioxidant compounds effective for augmenting oxidative stability of the base lipid are provided. Also provided are methods for enhancing the oxidative stability of a lipid comprising supplementing a base lipid in need of enhanced oxidative stability with at least one 1-(3-methoxybenzyl)-3-substituted thiourea compound of the present invention.

10 Claims, No Drawings

OTHER PUBLICATIONS

A. Mustafa et al. "Reaction of Thiourea with Hydrogen Peroxide: Carbon–13 NMR Studies of an Oxidative/Reductive Bleaching Process," Text. Res. J. 62(2), 94–100 (1992).

Internet "Uses of Meadowfoam Seed Oil™," Mar. 9, 2000, http://www.meadowfoam.com/uses/htm.

T. Abbott et al. "Antioxidants from Meadowfoam Stabilizes Other Oils," Abstract, Assoc. for the Adv. of Ind. Crops, Oct. 15–17, 2000, St. Louis, MO.

U.S. patent application Ser. No. 09/840,768, Abbott et al., filed Apr. 23, 2001.

U.S. patent application Ser. No. 09/725,560, Wohlman, filed Nov. 29, 2000.

$89^{th}$ Am. Oil Chem. Soc., May 10–13, 1998, Chicago, Illinois. This presentation discussed some of the compounds that are present in crude meadowfoam seed oil that do not contribute substantially to the oxidative stability of lipids or oils. It did not discuss any 1–(3–methoxybenzyl)–3–substituted thiorea compounds.

Assoc. for the Adv. of Ind. Crops, Oct. 15–17, 2000, St. Louis, MO. This presentation identified the presence of 1,3–di(3–methoxybenzyl) thiourea in meadowfoam seed oil. No other 1–(3–methoxybenzyl)–3–substituted thiourea compounds were discussed.

* cited by examiner

3-METHOXYBENZYL THIOUREA DERIVATIVES AND IMPROVED LIPID COMPOSITIONS CONTAINING SAME

This application is a continuation-in-part application of pending nonprovisional application U.S. Ser. No. 09/840,768, filed on Apr. 23, 2001, from provisional application U.S. Ser. No. 60/202,562, filed on May 10, 2000, both of which are incorporated by reference in their entireties herein.

FIELD OF THE INVENTION

This invention relates to novel 1-(3-methoxybenzyl)-3-substituted thiourea compounds and lipid and oil compositions supplemented with such compounds having enhanced oxidative stability.

BACKGROUND OF THE INVENTION

Natural lipids and oils are used in pharmaceutical preparations, food products, cosmetics, and various industrial products such as lubricants, coatings, inks, paints, plastics and the like. Such lipids are subject to oxidative degradation which can affect color, odor, viscosity, and lubricity characteristics thereof, adversely affecting the quality of the commercial products containing such lipids. In the food, cosmetics and pharmaceutical industries, maintaining high quality color and odor of oils and other lipids is important to avoiding oxidation-induced rancidity which is affected by factors such as the oxygen concentration, light and heat, as well as the degree of unsaturation of the lipid or oil, and the amount of natural or synthetic antioxidants present therein. Biodegradable lipids, oils and derivatives thereof used as cutting lubricants are recognized to be adversely affected by heat-induced oxidation.

Meadowfoam (*Limnanthes alba*) seed oil has been demonstrated to be highly stable to oxidation. It is more oxidatively stable than other vegetable oils. Although the identity of the compound(s) responsible for exceptional oxidative stability of meadowfoam seed oil is heretofore unknown, mixing meadowfoam seed oil with other oils imparts enhanced oxidative stability to the resulting mixtures. (Isbell, T. A., Abbott, T. A. and Carlson, K. D., 1999, "Oxidative Stability Index of Vegetable Oils in Binary Mixtures with Meadowfoam Oil," Ind. Crops Prod. 9(2): 115–123). Several minor constituents in meadowfoam seed oil which either diminish oxidative stability or impart small increases in oxidative stability of meadowfoam seed oil are known, however. (Abbott, T. P. and Isbell, T. A., 1998, Abstracts of the 89th American Oil Chemist's Society Annual Meeting & Expo, Chicago, Ill., May 10–13, p 66). Refined meadowfoam seed oil (and other refined seed oils and vegetable oils) exhibit reduced oxidative stability as a result of the refining process. After processing, meadowfoam seed oil has been shown to contain glucolimnanthin, a glucosinolate, and its degradation products 3-methoxyphenyl actetonitrile, 3-methoxybenzyl isothiocyanate and 3-methoxybenzaldehyde. (Vaughn, S. F., Boydston, R. A. and Mallory-Smith, C. A., 1996, "Isolation and Identification of (3-Methoxyphenyl) Acetonitrile as a Phytotoxin from Meadowfoam (*Limnanthes alba*) Seedmeal," J. Chem. Ecol. 22, 1939–1949). Glucosinolates have been shown to have little or no antioxidant effects. (Plumb, G. W., Lambert, N., Chambers, S. J., Wanigatunga, S., Heaney, R. K., Plumb, J. A., Aruoma, O. I., Halliwell, B. and Miller, N. J., 1996, "Are Whole Extracts and Purified Glucosinolates from Cruciferous Vegetables Antioxidants?" Free Rad. Res. 25, 75–86). When added to refined meadowfoam seed oil at levels from about 0.1% to 1.0%, the other compounds exhibit only small to moderate antioxidative effects, at best.

Thiourea has been shown to possess antioxidative activity in oils (Kajimoto and Murakami Nippon Eiyo, Shokuryo Gakkaishi 51(4):207–212, 1998; Chemical Abstract 129:188538); but thiourea is not very soluble in oils. The oxidative stability of ester-based synthetic lubricants (i.e., not vegetable oils) stabilized with amine antioxidants has been shown to be enhanced with specific thioureas (Chao T. S. and Kjonaas, M., "Some Synergistic Antioxidants for Synthetic Lubricants," Amer. Chem. Soc. Preprints, Div. Pet. Chem. 27(2):362–379, 1982). Camenzind and Rolf, Eur. Pat. Appl. EP 91-810474, Chemical Abstract 117:30273, show that certain acylated thioureas are able to increase the oxidative stability to lubricants and hydraulic fluids. Vegetable oils may be stabilized by other alkyl- and aryl-substituted thioureas that are not plant derived, as well (Martin, G. D., "Stabilization of Fatty Acid Compounds," 1939, U.S. Pat. No. 2,154,341).

Mono- and di-substituted thiourea compounds also have been described in U.S. Pat. Nos. 2,662,096, 3,852,348 and 3,991,008. Migirab et al., "Isothiocyanates, thioureas and Thiocarbamates Extracted from *Pentadiplandra brazzeanna*," Phytochem. 16(11): 1719–1721, (1977), disclose methoxy-substituted aromatic thioureas, such as N,N'-bis[(4-methoxyphenyl)methyl]-thiourea (CAS #22313-70-8) and N,N'-di(4-methoxybenzyl)thiourea, which were isolated in extracts from *Pentadiplandra brazzeana*.

Properties beneficial for commercial applications of lipid antioxidants include antioxidant activity in oils, thermal stability, low toxicity and lipid solubility. If the antioxidant will be employed in a sunscreen formulation for the skin and or hair, UVA and UVB absorbence activities of the antioxidant are also a benefit. Further, a thorough scientific characterization of the antioxidant compounds should include an elemental analysis, as well as NMR and IR spectral data.

There is a need for antioxidant compounds and compositions, especially natural antioxidants or derivatives thereof, that are soluble in lipids and oils, that are capable of imparting oxidative stability thereto when added at low concentrations, that exhibit thermal stability, that are not toxic and/or that absorb UVA and UVB wavelengths of sunlight.

Antioxidant compounds within the present invention are capable of imparting oxidative stability to lipids and/or oils when added at low concentrations, and are soluble in lipids and oils, exhibit thermal stability, are not toxic and/or absorb UVA and/or UVB wavelengths of sunlight. 1,3-di(3-methoxybenzyl)thiourea, for example, appears to have many of the qualities that are beneficial for an effective lipid antioxidant.

SUMMARY OF THE INVENTION

We have now unexpectedly discovered that excellent oxidative stability may be imparted to lipids and oils by compounds of the formula I:

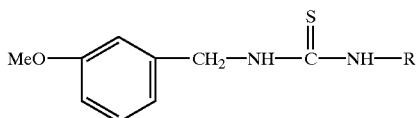

wherein R is a $C_1$–$C_{20}$ linear or branched alkyl, such as methyl, ethyl, propyl, isopropyl, butyl, isobutyl, tert-butyl, pentyl, hexyl, octyl, decyl, nonyl, dodecyl, and the like, $C_5$–$C_7$ cycloalkyl, such as cyclopentyl, cyclohexyl or cycloheptyl and the like, hydroxy- or -alkoxy-substituted $C_5$–$C_7$ cycloalkyl, $C_1$–$C_{20}$ linear or branched alkenyl, such as propenyl, butenyl or octadecenyl and the like, $C_5$–$C_7$ cycloalkenyl, $C_6$–$C_7$ aryl, such as phenyl or benzyl and the like, hydroxy- or alkoxy-substituted $C_6$–$C_7$ aryl, such as hydroxyphenyl, methoxyphenyl, ethoxyphenyl, hydroxybenzyl, methoxybenzyl or ethoxybenzyl and the like, benzoyl or hydroxy- or alkoxy-substituted benzoyl. Among compounds of the formula I, a presently preferred compound is 1,3-di(3-methoxybenzyl) thiourea, that is a compound of such formula I where R is a 3-methoxybenzyl moiety. An amount of a compound of formula I sufficient to impart oxidative stability to a lipid or oil (or compositions containing such lipids or oils) is from about 0.01 wt. % to about 5.0 wt. % based on the total weight of the lipid or oil.

The present invention also provides oxidatively stable lipid compositions comprising from about 95 wt. % to about 99.99 wt. % of a base lipid or oil and between about 0.01 wt. % and about 5.0 wt. %, more preferably between about 0.05 wt. % and 2.0 wt. %, and most preferably between about 0.1 wt. % and 1.0 wt. % of a compound of formula I. Lipids or oils of the present invention containing between about 3 wt. % and about 5 wt. % or more of a substituted thiourea compound of formula I, based on the total weight of the base lipid or oil composition, may be used as "concentrates" and conveniently added to processed seed oils or other lipids in need of enhanced oxidative stability to provide a lipid or oil composition of the present invention.

The present invention further provides a method for imparting oxidative stability to a base lipid or oil composition in need of enhanced oxidative stability, comprising the step of supplementing a base lipid or oil with an amount of a compound of formula I sufficient to impart enhanced oxidative stability to the base lipid or oil.

Presently preferred compounds of formula I are 1,3-di(3-methoxybenzyl)thiourea; 1-(3-methoxybenzyl)-3-ethyl-2-thiourea; 1-(3-methoxybenzyl)-3-propyl-2-thiourea; 1-(3-methoxybenzyl)-3-hexyl-2-thiourea; 1-(3-methoxybenzyl)-3-octadecyl thiourea; 1-(3-methoxybenzyl)-3-dodecyl-2-thiourea; 1-(3-methoxybenzyl)-3-octyl thiourea; 1-(3-methoxybenzyl)-3-(1-propenyl)thiourea; 1-(3-methoxybenzyl)-3-(4-hydroxyphenyl)-2-thiourea; 1-(3-methoxybenzyl)-3-benzyl thiourea; 1-(3-methoxybenzyl)-3-(3-methoxyphenyl)-2-thiourea and 1-(3-methoxybenzyl)-3-(4-methoxybenzoyl)thiourea. 1,3-di(3-methoxybenzyl) thiourea, which the inventors have identified as a significant natural antioxidant in meadowfoam seed oil, and in meadowfoam seed oil by-products, is a particularly preferred compound of the invention. 1,3-di(3-methoxybenzyl) thiourea from meadowfoam seed oil or meadowfoam seed oil by-products, or synthesized directly, appears to have many of the qualities that are beneficial for an effective lipid antioxidant.

It also has been surprisingly found that compounds of formula I, in combination with a benzylamine compound such as N-substituted benzylamines, exhibit a synergistic oxidative stabilizing effect in lipids and oils. Various naturally-occurring lipids and oils, such as seed oils and vegetable oils, contain benzylamine compounds. In these cases, the synergistic effect may be obtained by supplementing such a base lipid or oil with a compound of formula I and, optionally, with an exogenously added benzylamine compound in an amount sufficient to impart yet a further enhancement in oxidative stability. Thus, another aspect of the present invention entails lipid compositions comprising (i) a compound of formula I and (ii) a benzylamine or N-substituted benzylamine compound to impart enhanced oxidative stability.

DETAILED DESCRIPTION OF THE INVENTION

The present invention may be understood more readily by reference to the following detailed description of the preferred embodiments of the invention, and to the examples included therein.

In one of its aspects, the present invention entails 1-(3-methoxybenzyl)-3-substituted thiourea compounds of the formula I:

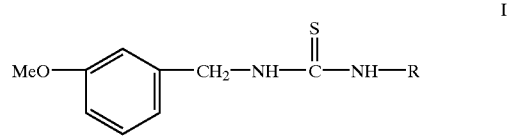

wherein R is selected from the group consisting of $C_1$–$C_{20}$ linear or branched alkyl; $C_5$–$C_7$ cycloalkyl; alkoxy-substituted $C_5$–$C_7$ cycloalkyl; hydroxy-substituted $C_5$–$C_7$ cycloalkyl; $C_1$–$C_{20}$ linear or branched alkenyl; $C_5$–$C_7$ cycloalkenyl; $C_6$–$C_7$ aryl; hydroxy-substituted $C_6$–$C_7$ aryl; alkoxy-substituted $C_6$–$C_7$ aryl; benzoyl; hydroxy-substituted benzoyl; and alkoxy-substituted benzoyl. In a particularly preferred embodiment, the substituted aryl moiety is a 3-hydroxy-substituted or 3-alkoxy-substituted aryl compound.

In another of its aspects, the present invention entails a lipid composition with enhanced oxidative stability comprising from about 95 wt. % to about 99.99 wt. % of a base lipid and from about 0.01 wt. % to about 5.0 wt. %, more preferably between about 0.05 wt. % and 2.0 wt. %, and still more preferably about 0.1 wt. % to about 1.0 wt. %, of a 1-(3-methoxybenzyl)-3-substituted thiourea compound of the formula I:

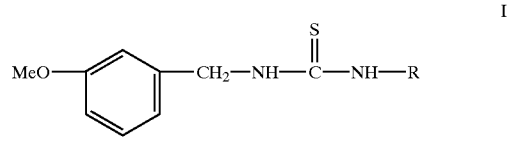

wherein R is selected from the group consisting of $C_1$–$C_{20}$ linear or branched alkyl; $C_5$–$C_7$ cycloalkyl; hydroxy- or alkoxy-substituted $C_5$–$C_7$ cycloalkyl; $C_1$–$C_{20}$ linear or branched alkenyl; $C_5$–$C_7$ cycloalkenyl; $C_6$–$C_7$ aryl; hydroxy- or alkoxy-substituted $C_6$–$C_7$ aryl; benzoyl; and hydroxy- or alkoxy-substituted benzoyl.

In a further of its aspects, the present invention entails a method of enhancing the oxidative stability of a lipid, comprising the step of combining a lipid with an oxidative stability-enhancing amount of a compound of the formula I:

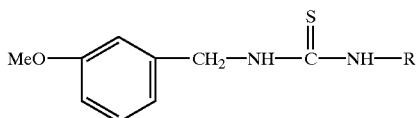

wherein R is selected from the group consisting of $C_1$–$C_{20}$ linear or branched alkyl; $C_5$–$C_7$ cycloalkyl; hydroxy- or alkoxy-substituted $C_5$–$C_7$ cycloalkyl; $C_1$–$C_{20}$ linear or branched alkenyl; $C_5$–$C_7$ cycloalkenyl; $C_6$–$C_7$ aryl; hydroxy- or alkoxy-substituted $C_6$–$C_7$ aryl; benzoyl; and hydroxy- or alkoxy-substituted benzoyl.

The compounds of the present invention may be added to essentially any lipid in which the compounds of the invention are soluble to augment the oxidative stability of such lipid. The term "lipid" as used herein includes vegetable oils, seed oils, triglycerides, waxes of triglycerides, and phospholipids. Among the lipids that may be supplemented with amounts of the compounds of the present invention to impart enhanced oxidative stability are vegetable oil, jojoba oil, sunflower oil, milkweed oil, peanut oil, corn oil, cottonseed oil, safflower oil, soybean oil, rapeseed (canola) oil, palm oil, olive oil, jojoba wax ester and lecithin. As used herein, the phrase "base lipid," "base oil" or equivalent phrase means a lipid or oil to which a compound of formula I has not been exogenously added.

As used herein, "$C_1$–$C_{20}$ linear or branched alkyl" shall include methyl, ethyl, propyl, isopropyl, butyl, isobutyl, t-butyl, pentyl, 2-methyl-pentyl, 3-methyl-penyl, hexyl, octyl, decyl, dodecyl, and the like. The term "$C_5$–$C_7$ cycloalkyl" shall include cyclopentyl, cyclohexyl and cycloheptyl. The term "hydroxy- or alkoxy-substituted $C_5$–$C_7$ cycloalkyl" shall include cyclopentyl, cyclohexyl and cycloheptyl moieties that are substituted with an hydroxy, methoxy, ethoxy, or propoxy group or the like. The term "$C_6$–$C_7$ aryl" shall include phenyl and benzyl. The term "hydroxy- or alkoxy-substituted $C_6$–$C_7$ aryl" shall include phenyl and benzyl moieties that are substituted with a hydroxy, methoxy, ethoxy or propoxy group or the like. The term "$C_1$–$C_{20}$ linear or branched alkenyl" shall include propenyl, butenyl, pentenyl, hexenyl, octenyl, decenyl, dodecenyl, octadecenyl and the like. The term "$C_5$–$C_7$ cycloalkenyl" shall include cyclopentenyl, cyclohexenyl and cycloheptenyl. The term "hydroxy- or alkoxy-substituted benzoyl" shall include a benzoyl moiety, as that term is defined in the art, that is substituted with an hydroxy, methoxy, ethoxy, or propoxy group or the like.

By use of the phrase "enhanced oxidative stability," "augmented oxidative stability" or an equivalent phrase, it is meant that a lipid composition of the invention has an increased ability to inhibit oxidation as measure by the Oxidative Stability Index (OSI) and/or by the Oxidative Stability by Rotating Pressure Vessel (RBOT) test disclosed herein, as compared to the base lipid or oil (i.e., one not supplemented with an exogenously added compound of formula I). It is presently preferred that a lipid or oil composition of the invention exhibit an OSI and/or RBOT value at least 10% greater, more preferably at least 100% greater, and most preferably at least about 200% greater or more than the OSI or RBOT value of the base lipid or base oil composition to which it is compared, when the OSI test is carried out at a temperature between about 110° C. and about 130° C., and the RBOT test is carried out under the conditions described herein.

The phrase "combining a lipid or oil with an oxidative stability-enhancing amount of a compound of formula I" as used herein includes the addition of a compound of formula I directly to the lipid or oil, as well as the addition to the lipid or oil of compounds that react therein to form a compound of formula I, for example 3-methoxybenzylamine and an isothiocyanate compound of the formula II (defined hereinbelow), preferably in a one to one ratio.

Compounds of the formula I may be synthesized by reacting 3-methoxybenzylamine and an appropriately selected isothiocyanate compound of the formula II S=C=N—R, wherein R is defined the same as for compounds of formula I. The reaction may be carried out by slowly adding the isothiocyanate to an aqueous solution of 3-methoxybenzylamine, preferably under a nitrogen atmosphere. The thiourea product of the reaction, which is a compound of formula I, may be recovered and purified by mixing the reaction products with a solvent that is not miscible with water but one that is a solvent for the thiourea, such as methylene chloride, chloroform, toluene or diethyl ether. The water layer may or may not be acidified to enhance separation and recovery of the thiourea compound of the invention. The thiourea, dissolved in the solvent layer, can be drawn off from the water layer, dried and the resulting crude thiourea purified by recrystallization in an appropriate solvent, such as ethanol. See the examples set forth hereinbelow. See also, generally, the procedure of Moore and Crossley, Organic Synthesis 2, 617–618 (note 4).

The reactants, 3-methoxybenzylamine and an appropriate isothiocyanate compound as defined above, may be obtained commercially or may be synthesized by routine methods known in the art, and the resultant product compounds of formula I may be readily isolated by routine methods well-known to those having ordinary skill in the art. Suitable isothiocyanate reactants for synthesizing compounds of the present invention may be obtained as well-known in the art from degradation of glucosinolates present in seed oils and other lipids. In an aqueous solution containing the enzyme thioglucosidase, glucosinolate compounds are degraded into isothiocyanates and other degradation products. See, Vaughn et al., 1996, "Isolation and Identification of (3-Methoxyphenyl) Acetonitrile as a Phytotoxin from Meadowfoam (*Limnanthes alba*) Seedmeal," J. Chem. Ecol. 22, 1939–1949; and C. VanEtten and H. Tookey, 1983, Glucosinolates, pp. 15–30 in M. Rechcigl (ed.) "Naturally Occurring Food Toxicants," CRC Press, Boca Raton, Fla. The isothiocyanate fraction of the glucosinolate breakdown products, thus, may be isolated and reacted with 3-methoxybenzylamine, as described above, to provide compounds of the present invention. Approximately 100 glucosinolate compounds have been identified in plants from 11 different plant families including mustard, rapeseed, cabbage, garlic mustard and crambe (S. F. Vaughn, 1999, "Glucosinolates as Natural Pesticides in Biologically Active Natural Products: Agrochemicals," H. G. Cutler and S. J.Cutler, Eds, CRC Press, Boac Raton, Fla.) Oils isolated from glucosinolate containing plants are normally deodorized by steam sparging to remove volatile compounds, which include isothiocyanates and amines. Thus, a variety of isothiocyanate compounds and benzylamine compounds may be obtained from the waste distillation products generated in the process of purifying such oils, and employed as reactants in synthesizing compounds of the present invention.

3-methoxybenzylamine may be purchased commercially, or may be isolated from meadowfoam oil, by extraction into an immiscible acidified aqueous layer which is separated from the oil, washed with a nonpolar solvent, treated with a base to lower pH, and the amine extracted into an immiscible solvent. The 3-methoxybenzylamine compound may be further purified by crystallization from ethanol or similar solvent and/or purified by reverse-phase HPLC using a C18 column, eluting with a gradient starting at 100% methanol and proceeding to about 80% methanol:20% chloroform. The peak containing 3-methoxybenzylamine may be identified by its retention time on the HPLC column in comparison to the retention time for a known standard sample of 3-methoxybenzylamine. Other natural amines may be purchased commercially, or may be similarly extracted from natural sources, and purified with reference to known standard samples and/or identified by standard chemical methods for identification of amines (e.g., chromatography, infrared spectroscopy, mass spectroscopy, elemental analysis, nuclear magnetic resonance analysis and the like).

The oxidative stability of a lipid, with and without addition of a compound of the present invention, may be determined by procedures that are described in the literature. See, for example, K. Tian and P. Dasgupta, Anal. Chem. 71, 1692–98 (1999).

A presently preferred method of determining oxidative stability of lipids and oils employs the Oxidative Stability Index (OSI), which determines the oxidative stability of an oil by passing air through a sample under stringent temperature control. (Firestone, Oxidative Stability Index (OSI): Official Methods of Recommended Practices of the American Oil Chemists' Society (AOCS), $4^{th}$ Ed. American Oil Chemists Society, Champaign, Ill., AOCS Official Method Cd 12b-92, 1993.) In this method, a stream of air is passed through the oil sample, which aids in the rapid degradation of the triglyceride into volatile organic acids. The air stream flushes the volatile acids from the oil into a conductivity cell containing water where the acids are solubilized. These acids, once dissolved in the water solution, disassociate into ions, thus changing the conductivity of the water. Therefore, a continuous measure of the conductivity of the cell by computer will indicate when a rapid rise in the conductivity occurs that corresponds to the induction point, oxidative failure of the sample. The time to the induction point is the OSI time. An AOCS standard method has been recently developed and a collaborative study has also been published (Jebe et al., J. Am. Oil Chem. Soc. 70, 1055–61 (1993)), demonstrating that the OSI method has good reproducibility among samples and laboratories. Saturated fatty acid methyl ester (FAME) standards commercially available from Alltech Associates (Deerfield, Ill.) may be used to calibrate the OSI determinations.

OSI determinations may be performed on an oxidative stability instrument manufactured by Omnion (Rockland, Mass.) using the AOCS method described in the above-disclosed Firestone reference. Lipid or oil samples may be run at 110° C. and FAMEs may be tested at 90° C., with air flow set at 35 kPa with a resulting velocity of about 140ml/min. A presently preferred method for determining OSI values is described by T. A. Isbell et al., "Oxidative Stability Index of Vegetable Oils in Binary Mixtures with Meadowfoam Oil," Industrial Crops and Products 9, 115–123 (1999).

Another presently preferred method of determining oxidative stability of lipids and oils employs the Oxidative Stability by Rotating Pressure Vessel (RBOT) test. In this test, oxidative stability, determined according to the ASTM D2272-98 test method (ASTM, 2001, "Standard Test Method for Oxidation Stability of Steam Turbine Oils by Rotating Pressure Vessel," in Book of Standards, Vol. 05.01., American Society for Testing and Materials, West Conshohocken, Pa.), measures the time for oxygen pressure to decrease in a closed stainless steel vessel containing a lipid or oil when heated with a copper coil catalyst. Oxygen taken up by the lipid or oil during the reaction is an indication of oil degradation.

Compounds of formula I may be conventionally mixed with a suitable lipid or oil and solubilized at concentrations up to 3.0%–5.0% or more. It is presently contemplated that concentrations of a compound of formula I between about 0.1% and 1.0% are sufficient to provide up to about 2-fold to 10-fold enhancement in oxidative stability of a base lipid or oil in need of enhanced oxidative stability. However, lipids or oils of the present invention containing up to 3.0%–5.0% of a compound of formula I are useful as "concentrates" that can be conveniently diluted up to 30- to 50-fold or more with a base lipid in need of enhanced oxidative stability. The base composition of such a concentrate may itself be a lipid or oil such as a seed oil or vegetable oil or a food grade solvent. Moreover, a compound of formula I, optionally in combination with an amine compound, such as 3-methoxybenzylamine, may be provided in an oil-in-water emulsion or a water-in-oil emulsion, or the like. The emulsions are presently contemplated to be especially useful as additives to biodegradable cutting lubricants, such as canola oil, soybean oil, vegetable oil estolyte, or other cutting lubricants, to enhance the oxidative stability of such lubricants.

In presently preferred embodiments of the lipid or oil compositions of the invention, the base lipid or oil is supplemented with an effective amount of a compound of formula I, e.g., a concentration of between about 0.1% and 1.0%, as well as a benzylamine compound present in an amount sufficient to augment the oxidative stability imparted by the compound of formula I. The amount of a benzylamine compound to be added to a lipid or oil composition of the invention may be determined by observing increases in OSI and/or RBOT values as a function of amount of the benzylamine compound added. While a base lipid or oil may inherently contain an amine compound, additional amounts of an amine compound, preferably 3-methoxybenzylamine, may be added to a lipid or oil that has been supplemented with a compound of formula I to increase the oxidative stability of such a lipid or oil composition of the present invention. The amount of such an amine compound to be added to a lipid or oil composition of the invention to achieve a synergistic anti-oxidation effect may be determined empirically by adding predetermined amounts of the amine compound to aliquots of the lipid or oil composition containing a compound of formula I and measuring the increase in OSI and/or RBOT value(s) obtained.

The following nonlimiting examples further describe and illustrate the methods for the preparation of the compounds and compositions of the invention, as well as the scientific characterization of synthesized compounds and the testing of synthesized compounds to determine their antioxidant activities, lipid solubility, thermal stability, toxicity and/or ability to absorb UVA and/or UVB light wavelengths. The examples are intended to be merely illustrative of the present invention, and not limiting thereof in either scope of spirit. Those of skill in the art will readily understand that variations of certain of the conditions and/or steps employed in the procedures described in the examples can be used to prepare and test these compounds and compositions.

All of the materials and equipment employed in the examples, and generally employed to make and test the compounds and compositions of the present invention, are commercially available from sources known by those of skill in the art. 3-methoxybenzyl isothiocyanate, 3-methoxyphenyl isothiocyanate and 4-methoxybenzoyl isothiocyanate were obtained from Transworld Chemicals (Rockville, Md.). Octadecylamine hydrochloride, dodecylamine, octylamine, allyl isothiocyanate, 3-methoxybenzyl amine, benzyl isothiocyanate and most of the other chemicals employed in the examples were obtained from Fisher Scientific (Pittsburgh, Pa.), and generally were reagent grade. Crude meadowfoam seed oil was obtained as approximately 50% oil in hexane solutions, and refined meadowfoam seed oil was obtained from the Fanning Corporation (Chicago, Ill.). Refined jojoba oil was obtained from Purcell Jojoba International, LLC (Avila Beach, Calif.), and high oleic sunflower oil was obtained from International Flora Technologies (Gilbert, Ariz.). Refined, bleached and deodorized soybean oil was obtained from Archer Daniels Midland (Decatur, Ill.), and refined milkweed oil was obtained from the United States Department of Agriculture (Peoria, Ill.).

Unless otherwise stated, all percentages described in the examples are weight percentages (wt. %).

Unless otherwise stated, Oxidative Stability Index (OSI) values were determined on 5.00±0.05 g lipid or oil samples in triplicate according to AOCS Official Method Cd 12b-92 (AOCS, 1993) at 90° C., 110° C. and/or 130° C. on an oxidative stability instrument manufactured by Omnion (Rockland, Mass.). Details of the procedure have been published by Isbell et al., "Oxidative Stability Index of Vegetable Oils in Binary Mixtures with Meadowfoam Oil," Ind. Crops Prod. 9, 115–123 (1999). When compounds of the present invention were added to the lipid or oil sample being tested, the compounds (0.1 % to 1.0% by weight) were added to the test lipid or oil (20 g) and dissolved or dispersed at room temperature before triplicate 5.00 g samples of lipid or oil with an added compound of the invention were weighed into the OSI test tube.

EXAMPLE 1

Identification and Testing of the Components of Crude Meadowfoam Seed Oil

Refined meadowfoam seed oil is a highly monounsaturated vegetable oil. Its oxidative stability is reduced during the refining processes.

Initial oxidative stability (OSI) tests indicated that crude meadowfoam seed oil had a greater oxidative stability (88.1 h at 130° C.) than refined meadowfoam seed oil (15.3 h at 130° C.), although the OSI value for the crude meadowfoam seed oil varied somewhat for oil collected from 1994–1997. Also, an initial study of various extracts of meadowfoam seed oil showed that the addition of 10% of the acetonitrile extract of crude meadowfoam seed oil could restore the oxidative stability of refined meadowfoam oil to 86.6 h at 130° C.

The acetonitrile extract of crude meadowfoam seed oil, and crude meadowfoam seed oil itself, were separated on preparative HPLC to yield fractions which were tested on GC-MS to tentatively identify their constituents. Volatile components of crude meadowfoam seed oil were separated by distillation under high vacuum in a Kugelrohr distillation apparatus.

A C18, 55–105 µm PrepPak Cartridge was used to separate the acetonitrile extract of crude meadowfoam seed oil and crude meadowfoam seed oil (3.0 or 5.0 g) on a LC 4000 system (Waters, Milford, Mass.) with a tunable UV detector set at 280 nm. The column was equilibrated with 60:40 isopropanol (solvent A):water (solvent B) at a 50 ml/min elution rate. This solvent ratio was continued after sample injection up to 6 min. A gradient from 60:40, A:B to 100% solvent A from 6 to 18 min was followed by 100% solvent A for 6 min, and then a gradient from 24 to 30 min to 100% solvent C (95:4:1 isopropanol:hexane:diethyl ether). Solvent C (100%) was added from 30–40 min, and then a gradient was used over 13 min to return to the initial solvent. The diethyl ether used in the HPLC had been washed with 0.1 N NaOH to remove any stabilizing phenolic antioxidants before use. Six samples were collected depending on observed peaks in the detector trace.

GC-MS was performed with a Hewlett-Packard (Palo Alto, Calif.) 5890A GC with a Supelco SSPB1 30 m×0.2 mm i.d. column and a Hewlett-Packard 5970 mass selective (EI) detector. The gas flow was electronically controlled to maintain a constant 1 ml/min flow rate. Injector and transfer line temperatures were set at 250° C. and 300° C., respectively, and the split was 20:1. A programmed temperature ramp of 70 to 345° C. at 10° C./min was used after a 1 µl sample injection.

The components identified by GC-MS of the HPLC and distillate fractions are set forth in Table 1 below.

TABLE 1

Compounds Determined to be Present in Unrefined (Crude) Meadowfoam Seed Oil in Addition to Triglycerides 3-methoxyphenyl acetonitrile
3-methoxybenzyl isothiocyanate
3-methoxybenzyldehyde
3-methoxybenzyl amine
3-hydroxy-3-methylbutanenitrile
alpha-tocopherol
gamma-tocopherol
beta-sitosterol
ergost-5-en-3-ol
C18:0, C18:1, C18:2 and C18:3 free fatty acids Distillation removed principally 3-methoxyphenyl acetonitrile and 3-methoxybenzyl isothiocyanate. Oxidative stability was not affected by removing volatile components.

Adding 0.1 to 1.0% by weight of several of the constituents identified in Table 1 to refined meadowfoam seed oil gave no or slightly increased OSI values at 130° C., except for the combination of 3-methoxybenzyl amine with 3-methoxybenzyl isothiocyanate, as is shown below in Table 2.

TABLE 2

Oxidative Stability Index of Meadowfoam Seed Oil and Meadowfoam Seed Oil Plus Additives at 130° C.

| Oil | Additive | OSI Time (Hours) |
|---|---|---|
| Crude Meadowfoam Seed Oil (1977) | None | 88.1 |
| Refined Meadowfoam Seed Oil (1977) | None | 15.3 |
| Refined Meadowfoam Seed Oil | 3-methoxybenzyl isothiocyanate, 0.1% | 19.1 |
| Refined Meadowfoam Seed Oil | 3-methoxybenzyl isothiocyanate, 0.5% | 22.9 |
| Refined Meadowfoam Seed Oil | 3-methoxybenzyl isothiocyanate, 1.0% | 24.0 |
| Refined Meadowfoam Seed Oil | 3-methoxybenzyl amine, 0.1% | 22.9 |
| Refined Meadowfoam Seed Oil | 3-methoxybenzyl amine, 0.5% | 27.3 |
| Refined Meadowfoam Seed Oil | 3-methoxybenzyl amine, 1.0% | 32.6 |

TABLE 2-continued

Oxidative Stability Index of Meadowfoam Seed Oil and Meadowfoam Seed Oil Plus Additives at 130° C.

| Oil | Additive | OSI Time (Hours) |
|---|---|---|
| Refined Meadowfoam Seed Oil | 3-methoxyphenyl acetonitrile, 0.1% | 18.6 |
| Refined Meadowfoam Seed Oil | 3-methoxyphenyl acetonitrile, 0.5% | 19.2 |
| Refined Meadowfoam Seed Oil | 3-methoxyphenyl acetonitrile, 1.0% | 19.9 |
| Refined Meadowfoam Seed Oil | 3-methoxybenzaldehyde, 0.1% | 17.5 |
| Refined Meadowfoam Seed Oil | 3-methoxybenzaldehyde, 0.5% | 17.4 |
| Refined Meadowfoam Seed Oil | 3-methoxybenzaldehyde, 1.0% | 18.9 |
| Refined Meadowfoam Seed Oil | 0.1% of 1:1 3-methoxybenzyl amine: 3-methoxybenzyl isothiocyanate | 43.5 |
| Refined Meadowfoam Seed Oil | 0.5% of 1:1 3-methoxybenzyl amine: 3-methoxybenzyl isothiocyanate | 160 |
| Refined Meadowfoam Seed Oil | 1.0% of 1:1 3-methoxybenzyl amine: 3-methoxybenzyl isothiocyanate | 187 |
| Refined Meadowfoam Seed Oil | 1,3-di(3-methoxybenzyl) thiourea, 0.1% | 49.8 |
| Refined Meadowfoam Seed Oil | 1,3-di(3-methoxybenzyl) thiourea, 0.5% | 159 |
| Refined Meadowfoam Seed Oil | 1,3-di(3-methoxybenzyl) thiourea, 1.0% | 172 |

HPLC fractions showing amine absorbencies in the 3200 cm$^{-1}$ region and free fatty acid carbonyl absorbencies at 1700 cm$^{-1}$ in the infrared spectra were further separated by partitioning between water and ether at pH 2, 5, 8 and 10. 3-methoxybenzyl amine, found in the GC-MS of the HPLC fraction, was isolated, as was 1,3-di(3-methoxybenzyl) urea.

In further experiments, 3-methoxybenzyl isothiocyanate, shaken for 2 h at 50° C. with buffers at pH 3, 5, 7, 8 and 10, was recovered quantitatively and unchanged. The identity of 1,3-di(3-methoxybenzyl) urea isolated from meadowfoam oil was determined by NMR and exact mass from high resolution mass spectroscopy. Although 1,3-di(3-methoxybenzyl) urea could possibly have come from the isolation procedure, or by oxidation of 1,3-(3-methoxybenzyl)thiourea, it was concluded that the reactivity of 3-methoxybenzyl isothiocyanate toward 3-methoxybenzyl amine was so great (Table 2) that 1,3-di(3-methoxybenzyl)thiourea would form in the crude oil because both were present as degradation products of the glucosinolate, glucolimnanthin. 1,3-di(3-methoxybenzyl) thiourea was made from the isothiocyanate, and the amine and its structure were confirmed by proton and carbon NMR. On the GC-MS, only 3-methoxybenzyl isothiocyanate and 3-methoxybenzyl amine were detected as peaks when 1,3-di(3-methoxybenzyl)thiourea was injected, indicating that 1,3-di(3-methoxybenzyl)thiourea breaks down into these two components under the GC-MS conditions. On analytical HPLC, a small peak at 9.57 min retention time in crude meadowfoam oil matched that of 1,3-di(3-methoxybenzyl) thiourea spiked into refined meadowfoam oil.

EXAMPLE 2

Analysis of Crude and Refined Meadowfoam Seed Oil By High Performance Liquid Chromatography Crude and refined meadowfoam seed oil were analyzed by high performance liquid chromatography (HPLC). The HPLC system consisted of a Thermo Separations Products (Freemont, Calif.) instrument with a P2000 binary pump and an AS2000 autosampler/injector coupled with an evaporative light-scattering detector (ELSD 500, Alitech Associates, Deerfield, Ill.). Samples were separated on a Dynamax silica column (25 cm.×4.6 mm, 60A, 8 μm) from Rainin Instrument Co. (Woburn, Mass.), with a gradient elution at 1 ml/min. The initial solvent consisted of 95:5 hexane:isopropanol for 2 min, with a gradient to 60:40 hexane:isopropanol from 2–10 min, returning to 95:5 hexane:isopropanol at 10.1 min and holding there for 4.9 min before the next sample injection.

Analysis of crude and refined meadowfoam oil by high performance liquid chromatography (HPLC) gave a peak at retention time 9.5 minutes in the crude but not the refined oil. The retention time for the 1,3-di(3-methoxybenzyl) thiourea compound, synthesized in the manner described in Example 3, below, was 9.575 to 9.613 in different concentrations. Also, an extract of crude meadowfoam oil with acetonitrile solvent was separated into its components by HPLC and one component was identified by mass spectroscopy, NMR and elemental analysis to be 1,3-di(3-methoxybenzyl)urea, an oxidized form of the thiourea synthesized in Example 3. Accordingly, 1,3-di(3-methoxybenzyl)thiourea is shown to be a natural component in crude meadowfoam oil when extracted from the seed and not refined.

EXAMPLE 3

Synthesis of 3-Methoxybenzyl Thiourea Compounds

Based on the preliminary findings described in Example 1 above, 1,3-di(3-methoxybenzyl)thiourea and several related thiourea compounds were synthesized from 3-methoxybenzyl isothiocyanate and selected amines, or from 3-methoxybenzyl amine and isothiocyanates which resulted from enzymatic degradation of glucosinolates in plants other than meadowfoam, with the goal of improving lipid solubility and/or UV absorbance. Allyl isothiocyanate occurs as a degradation product of sinigrin in mustard, cabbage, broccoli and horseradish. Benzyl isothiocyanate occurs as a degradation product of glucosinolates in papaya. The occurrence of glucosinolates in cruciferous plants is believed to be one reason for the healthful effects of the plants in diets (Nijhoff W. A., Grubben, M. J. A. L., Nagengast, F. M., Jansen, J. B. M. J., Verhagen, H., van Poppel, G., Peter, W. H. M., 1995, "Effects of Consumption of Brussels Sprouts on Intestinal and Lymphocytic Glutathione S-Transferases in Humans," Carcinogenesis 16, 2125–2128).

These experiments were conducted to identify antioxidants in meadowfoam oil, and to determine their properties, and to synthesize structurally-related compounds to compare to compounds present in meadowfoam seed oil exhibiting antioxidant activity. Compounds isolated from meadowfoam seed oil (Limnanthes alba) were concluded to be either a source of 1,3-di(3-methoxybenzyl)thiourea or oxidation products from this compound. 3-methoxybenzyl isothiocyanate and 3-methoxybenzyl amine, which were identified in the meadowfoam seed oil as degradation products of the glucosinolate glucolinmanthin, reacted readily to form 1,3-di(3-methoxybenzyl)thiourea in meadowfoam seed oil, water and ethanol. 1,3-di(3-methoxybenzyl)urea, the oxygenated form of 1,3-di(3-methoxybenzyl)thiourea, was isolated from crude meadowfoam seed oil. 1,3-di(3-methoxybenzyl)thiourea and other disubstituted thioureas containing at least one 3-methoxybenzyl substituent were made from isothiocyanates and amines. 1,3-di(3-methoxyphenyl)urea and 1,3-di(3-methoxyphenyl)thiourea were also made to compare the effects of oxygen versus sulfur substitution on properties and the spatial effects of the methylene group in benzyl compared to phenyl substitution on properties of disubstituted thioureas.

The lipid solubility, antioxidant properties, toxicity ($LC_{50}$), stability and spectral absorbance properties of some of the above-described compounds were determined, and are discussed in other examples set forth hereinbelow.

Elemental analyses were performed by Desert Analytics (Tucson, Ariz.).

EXAMPLE 3(a)

1,3-Di(3-Methoxybenzyl)Thiourea

This example demonstrates the synthesis of 1,3-di(3-methoxybenzyl)thiourea in both water and ethanol.

In Water

To a three neck, 100 ml flask fitted with a condenser, a rubber syringe septum and a nitrogen inlet was added 20 ml water and 3.6 g (25.8 mmol) of 3-methoxybenzyl amine. The reaction vessel was purged with nitrogen and stirred with a teflon-coated magnetic stir bar. 3-methoxybenzyl isothiocyanate 2.59 ml (3.0 g, 16.7 mmol) was added dropwise (~1 drop/5–10 s) from a glass syringe. A separate layer formed and the mixture was stirred for 1 h at room temperature. The water layer was acidified with 1 M HCl (about 10 ml) to pH 5.5. Methylene chloride (15 ml) was added and the two layers were transferred to a separator funnel. The lower layer (methylene chloride) was removed. The water layer was washed with methylene chloride, twice more with 10 ml methylene chloride, and the combined $CHCl_2$ solutions were washed with 0.1 M HCl and then water. The $CHCl_2$ solution was dried over 3A molecular sieves and then evaporated to dryness in a rotating solvent evaporator. The resulting viscous liquid was taken up in 20 ml ethanol that had been heated to 35° C. and the product recrystallized by cooling in a refrigerator twice from ethanol as white crystals, dried in vacuum at room temperature and weighed. A second recrystallization was made from the mother liquor to retrieve additional product for a yield of 79.8% in the first crystal batch and 83.2% for the combined batches of crystals. Analysis of the product by NMR, mass spectroscopy and elemental analysis revealed the product to be 1,3-di(3-methoxybenzyl)thiourea.

The steps in the preceding paragraph were performed in the same manner a second time. This time, however, the condenser had a loose stopper to close the system, the amount of 3-methoxybenzyl amine added to the three-neck flask was 3.66 g (26.7 mmol), the amount of 3-methoxybenzyl isothiocyanate added dropwise from the glass syringe was 3.04 g (16.7 mmol), and the product was recrystallized by cooling at 4° C. twice from ethanol as white crystals. A second recrystallization was made from the mother liquor to retrieve additional product for a yield of 79.8% in the first crystal batch and 83.2% for the combined batches of crystals. Analysis of the product by NMR, mass spectroscopy and elemental analysis revealed the product to be 1,3-di(3-methoxybenzyl)thiourea. Calculated elemental analysis of 1,3-di(3-methoxybenzyl)thiourea: C, 64.53; H, 6.37; N, 8.85; S, 10.13. Found: C, 64.55; H, 6.37; N, 8.85; S, 10.17.

In Ethanol

To the same reaction vessel described in the preceding paragraph was added 4.05 g (29.5 mmol) of 3-methoxybenzyl amine in 83 ml of absolute ethanol. The flask was immersed in a 40° C. constant temperature bath, stirred and purged as before. 3-methoxybenzyl isothiocyanate (5.10 g, 28.5 mmol) was added in a 2 min period by syringe. Aliquots (1 ml) were removed and reacted with 1 ml concentrated $NH_4OH$ at 40° C. for 5 min and then frozen until testing. After 115 min, the reaction mixture was decanted into a beaker and cooled to −10° C. Crystals were filtered from the supernatant through Whatman 54 filter paper on a Buchner funnel. The yield was 7.5359 g of 1,3-di(3-methoxybenzyl)thiourea or 92% of theoretical after accounting for 0.612 g of reactants removed for testing. Calculated elemental analysis of 1,3-di(3-methoxybenzyl) thiourea: C, 64.53; H, 6.37; N, 8.85; S, 10.13. Found: C, 64.60; H, 6.42; N, 8.88; S, 10.08.

A test mixture of 50 $\mu l$ of 3-methoxybenzyl isothiocyanate in 0.9 ml ethanol with 1 ml concentrated $NH_4OH$ was completely reacted to monosubstituted 3-methoxybenzyl thiourea in less than 5 min based on thin-layer chromatography (TLC) analysis. TLC was performed on silica gel plates (Silica gel 60 F254, 250 $\mu m$ layer, EM Science, Gibbstown, N.J.) in 70:30:1 hexane:ethanol:acetic acid. $R_f$ values were 0.26 for 3-methoxybenzyl thiourea, 0.04 for 3-methoxybenzyl amine, 0.41 for 1,3-di(3-methoxybenzyl) thiourea and 0.63 for 3-methoxybenzyl isothiocyanate. Aliquots of the reaction taken from 6.5 min to 20 min after mixing of the 3-methoxybenzyl amine and 3-methoxybenzyl isothiocyanate showed minor traces of monosubstituted thiourea from unreacted 3-methoxybenzyl isothiocyanate and $NH_4OH$, but none could be detected 30 min after mixing 3-methoxybenzyl isothiocyanate and 3-methoxybenzyl amine.

The reaction of 3-methoxybenzyl isothiocyanate with 3-methoxybenzyl amine in ethanol was repeated doubling the reaction volume and reactants and heating for 2 h at 40° C. Crystallization at −10° C., followed by evaporation of the supernatant to 20 ml and a second crystallization gave 98.4% of the theoretical yield for the two crystallizations combined. Calculated elemental analysis of 3-methoxybenzyl thiourea: C, 64.53; H, 6.37; N, 8.85; S, 10.13. Found: C, 64.30; H, 6.46; N, 8.85; S, 10.09.

EXAMPLE 3(b)

1-(3-Methoxybenzl)-3-Octadecyl Thiourea

This example demonstrates the synthesis of 1-(3-methoxybenzyl)-3-octadecyl thiourea.

Octadecyl amine hydrochloride was converted to the amine by mixing an ether solution of the amine hydrochloride with 1 M NaOH, separating and evaporating the ether layer, dissolving the amine in $CHCl_3$, filtering through Whatman 541 filter paper and evaporating the $CHCl_3$. Octadecyl amine (5.9252 g, 22.0 mmol) in 150 ml ethanol was reacted with an excess (4.32 g, 24.1 mmol) of 3-methoxybenzyl isothiocyanate at 40° C. under $N_2$ with stirring. Excess isothiocyanate was used because co-crystallization of octadecyl amine is difficult to prevent when an excess of amine is present. After 2 h the solution was cooled to 4° C., centrifuged at 10,000 rpm for 20 min and the precipitated crystals were washed with ethanol (20 ml). The combined supernatant and wash was evaporated to 20 ml total volume and then cooled to −10° C. to filter off a second batch of crystals. The supernatant was dried and 94.3% of reagents weight was recovered, 74.9%, or 7.40 g as 1-(3-methoxybenzyl)-3-(octadecyl)thiourea of about 76% purity based on the sulfur analysis. The octadecyl amine was difficult to separate from the thiourea by crystallization.

Calculated elemental analysis of 1-(3-methoxybenzyl)-3-octadecyl thiourea: C, 72.27; H, 10.78; N, 6.24; S, 7.15. Found: C, 71.96; H, 11.00; N, 5.95; S, 5.46. A recrystallization from acetone/chloroform gave crystals with the composition: C, 72.37; H, 10.98; N, 6.13; S, 6.92.

EXAMPLE 3(c)

1-(3-Methoxybenzyl)-3-Dodecyl Thiourea

This example demonstrates the synthesis of 1-(3-methoxybenzyl)-3-dodecyl thiourea.

Dodecyl amine (4.89 g, 26.4 mmol) in 83 ml ethanol at 50° C. was reacted with 3-methoxybenzyl isothiocyanate (3.97 g, 22.1 mmol) for 6 h under $N_2$ with stirring, and then poured into a 250 ml beaker. Performing this reaction at 40° C. led to a precipitate that was difficult to stir. Crystallization began as soon as the reaction started cooling below 50° C. The reaction mixture was cooled to 4° C. and the crystals were filtered off using Whatman 54 filter paper. The crystals were washed with 15 ml of ethanol. Combined filtrates were evaporated to dryness and taken up in 10 ml ethanol. Cooling the solution to −10° C. gave no crystals. The solution was evaporated to dryness and the solids were weighed. Material recovery was 98.7%, and yield of crystals was 7.62 g, or 94.4% of the theoretical yield. Calculated elemental analysis of 1-(3-methoxybenzyl)-3-dodecyl thiourea: C, 69.18; H, 9.95; N, 7.68; S, 8.79. Found: C, 69.65; H, 10.07; N, 7.67; S, 8.80.

EXAMPLE 3(d)

1-(3-Methoxybenzyl)-3-Octyl Thiourea

This example demonstrates the synthesis of 1-(3-methoxybenzyl)-3-octyl thiourea.

N-Octyl amine (3.09 g, 23.9 mmol) in 83 ml ethanol at 40° C. was reacted with an excess of 3-methoxybenzyl isothiocyanate (4.7 g, 26.2 mmol) for 2 h under $N_2$ with stirring, then transferred to a 100 ml beaker, cooled to 4° C. and the crystals filtered off using Whatman 541 filter paper. The filtrate was evaporated to 20 ml and cooled to 4° C. to obtain a second crop of crystals. The remaining supernatant was dried and weighed. The first and second crop of crystals yielded 6.32 g, or 85.5% of the theoretical amount of 1-(3-methoxybenzyl-3-octyl thiourea. Calculated elemental analysis of 1-(3-methoxybenzyl)-3-octyl thiourea: C, 66.19; H, 9.15; N, 9.08; S, 10.39. Found: C, 66.21; H, 9.04; N, 9.07; S, 10.59.

EXAMPLE 3(e)

1-(3-Methoxybenzyl)-3-(1-Propenyl)Thiourea

This example demonstrates the synthesis of 1-(3-methoxybenzyl)-3-(1-propenyl)thiourea.

3-methoxybenzyl amine (9.81 g, 71.5 mmol) in 160 ml ethanol, at 40° C., was reacted with allyl isothiocyanate (7.55 g, 94% purity, 71.6 mmol) for 2 h under $N_2$ with stirring, after which the mixture was cooled to −10° C. No crystals formed and the solvent was evaporated at 50° C. on a rotating solvent evaporator under vacuum. A yellow viscous liquid resulted and it hardened to a waxy solid at 4° C. The waxy solid was washed with hexane and dried at room temperature under vacuum. A second experiment with 14% excess amine gave an 81.4% yield of a white waxy partially crystalline, partially liquid mix at 4° C. which was a liquid at room temperature. Calculated elemental analysis of 1-(3-methoxybenzyl)-3-(1-propenyl)thiourea: C, 60.99; H, 6.82; N, 11.85; S, 13.57. Found: C, 60.77; H, 6.70; N, 11.68; S, 13.96.

EXAMPLE 3(f)

1-(3-Methoxybenzyl)-3-Benzyl Thiourea

This example demonstrates the synthesis of 1-(3-methoxybenzyl)-3-benzyl thiourea.

3-methoxybenzyl amine (4.94 g, 36.0 mmol) in 80 ml hexane, at 40° C., was reacted with benzyl isothiocyanate (5.29 g, 35.5 mmol) for 2 h under $N_2$ with stirring, after which the mixture was cooled to 4° C. Two layers formed and the upper hexane layer was decanted. After removing traces of hexane under vacuum at room temperature, a viscous liquid remained. Addition of 8 ml ethanol gave a clear solution which crystallized at 4° C. The crystals were dried at room temperature under vacuum to give a 9.30 g (91.7% of theoretical) yield. Calculated elemental analysis of 1-(3-methoxybenzyl)-3-benzyl thiourea: C, 67.10; H, 6.34; N, 9.78; S, 11.20. Found: C, 67.17; H, 6.22; N, 9.70; S, 11.08.

EXAMPLE 3(g)

1-(3-Methoxybenzyl)-3-(4-Methoxybenzoyl) Thiourea

This example demonstrates the synthesis of 1-(3-methoxybenzyl)-3-(4-methoxybenzoyl)thiourea.

3-methoxybenzyl amine (9.84 g, 71.7 mmol) in 160 ml ethanol, at 40° C., was reacted with 4-methoxybenzoyl isothiocyanate (15.09 g, 78.1 mmol) for 2 h under $N_2$ with stirring, after which the mixture was cooled to 4° C. Crystals formed overnight and the supernatant was decanted. Some, but not all, crystals redissolved at 53° C. in 150 ml ethanol. Insoluble crystals were filtered off and the ethanol was cooled to 4° C. to recover a twice crystallized batch of crystals. All supernatants were combined and evaporated to 20 ml and then cooled to 4° C. to recover a third batch of crystals. The supernatant was evaporated to dryness and the solids were weighed. The combined recovery was 95.0% of starting material and the crystalline material from the three crystallizations was 19.5 g or 82.3% of the theoretical yield. Calculated elemental analysis of 1-(3-methoxybenzyl)-3-(4-methoxybenzoyl)thiourea: C, 61.80; H, 5.49; N, 8.48; S, 9.70. Found: C, 61.88; H, 5.39; N, 8.85; S,9.79.

Infrared spectra were collected on a BOMEM MB Series spectrophotometer (ABB BOMEM, Quebec, QC) with Grams 32 software under a dry, $CO_2$— free air purge. Thirty-two co-added scans at 4 $cm^{-1}$ resolution were collected for smears and finely ground crystals between NaCl discs. $^1H$ NMR and $^{13}C$ NMR spectra were obtained on a Bruker DRX 400 (Karlsruhe, Germany) with a 5-mm dual proton/carbon probe (400 MHz $^1H$/100.61 MHz $^{13}C$). $CDCl_3$ was used as solvent for all thiourea samples and hexadeutero dimethylsulfoxide for substituted ureas.

Infrared spectra proved to be useful for rapid confirmation of product formation. Isothiocyanate absorbances at 2175 $cm^{-1}$ and 2095 $cm^{-1}$ disappeared in the reaction products spectra, and the thiourea carbonyl absorbances at 1550±5 $cm^{-1}$ were well separated from aromatic ring absorbances at 1602–1606 $cm^{-1}$. The monosubstituted thiourea carbonyl also absorbed at 1547 $cm^{-1}$, but it could be differentiated from the disubstituted thiourea by the —$NH_2$ absorbances at 3280 $cm^{-1}$ and 3181 $cm^{-1}$, compared to a single —NH absorbance at 3260–3280 $cm^{-1}$. Crystals of the aromatic-aliphatic disubstituted thioureas 1-(3-methoxybenzyl)-3-octadecyl thiourea, 1-(3-methoxybenzyl)-3-dodecyl thiourea and 1-(3-methoxybenzyl)-3-octyl thiourea, had two different N—H absorbances at about 3240 and 3306 $cm^{-1}$, probably from their very different substituents, benzyl and n-alkyl. A common characteristic of the 3-methoxybenzyl substituent was the C—H absorbance of the methoxy at 2836 cm$^{-1}$ and the aromatic substitution pattern absorbances most often seen at 850–880 cm$^{-1}$ (Ar C—H with adjacent substituted carbons), 782 cm$^{-1}$ (3 adjacent Ar C—H) and 692 cm$^{-1}$ (typical of meta or 1,3 substitution).

NMR ($^{13}$C and $^1$H) confirmed the identity of prepared and isolated compounds. The NMR results are set forth below in Tables 3 and 4 hereinbelow.

In each of Tables 1 and 3, compound 1 represents 1,3-di (3-methoxybenzyl)thiourea, compound 2 represents 1-(3-methoxybenzyl)-3-octadecyl thiourea, compound 3 represents 1-(3-methoxybenzyl)-3-dodecyl thiourea, compound 4 represents 1-(3-methoxybenzyl)-3-octyl thiourea, compound 5 represents 1-(3-methoxybenzyl)-3-(l-propenyl)-thiourea, compound 6 represents 1-(3-methoxybenzyl)-3-benzyl thiourea and compound 7 represents 1-(3-methoxybenzyl)-3-(4-methoxybenzoyl)thiourea.

In Table 3, for each of compounds 1–7, carbon numbers 1–7 correspond to the carbon atoms of the 3-methoxtbenzyl moiety on the left side of formula 1, with number 7 representing the carbon atom of the —CH$_2$— group attached to the 1 position of the aromatic ring. Number 3 represents the carbon atom present in the methoxy group. Numbers 2 and 4–6 represent other carbon atoms present in the aromatic ring, going around the ring from carbon atom number 1 towards carbon atom number 3. For compound 1, numbers 1'–7' correspond to the carbon atoms of the 3-methoxtbenzyl moiety on the right side of the compound, with the number 7' representing the carbon atom of the —CH$_2$— group attached to the 1' position of the aromatic ring. Number 3' represents the carbon atom of the methoxy group present on this ring. Numbers 2' and 4'–6' represent other carbon atoms present in the aromatic ring, going around the ring from carbon atom number 1 towards carbon atom number 3. For compound 2, number 1' represents the carbon atom of the —CH$_2$— group on the right side of the molecule bonded to the —NH— group of the —CS—NH— moiety, and number C18' represents the carbon atom of the —CH$_3$ group attached at the end of the —(CH$_2$)$_{17}$— group. Numbers 2', 3', C4'–C15', C16' and C17' represent the carbon atoms in between the 1' and the C18' carbon atoms, numbering in order from 1 to 18. For compound 3, number 1' represents the carbon atom of the —CH$_2$— group on the right side of the molecule bonded to the —NH— group of the —CS—NH— moiety, and number C12' represents the carbon atom of the —CH$_3$ group attached at the end of the —(CH$_2$)$_{11}$— group. Numbers 2', 3', 4', 5'6', C7'-C9', C10' and C11' represent the carbon atoms in between the 1' and the C12' carbon atoms, numbering in order from 1 to 12. For compound 4, number 1' represents the carbon atom of the —CH$_2$— group on the right side of the molecule bonded to the —NH— group of the —CS—NH— moiety, and number 8' represents the carbon atom of the —CH$_3$ group attached at the end of the —(CH$_2$)$_7$— group. Numbers 2', 3', 4', 5', 6' and 7' represent the carbon atoms in between the 1' and the 8' carbon atoms, numbering in order from 1 to 8. For compound 5, number 1' represents the carbon atom of the —CH$_2$— group on the right side of the molecule bonded to the —NH— group of the —CS—NH— moiety. The 2' represents the carbon atom of the —CH= group attached to this —CH$_2$— group, and the 3' represents the carbon atom of the =CH$_2$ group. For compound 6, numbers 1', 2', C3'–C5', 6' and 7' correspond to the carbon atoms of the benzyl moiety on the right side of the compound, with the number 7' representing the carbon atom of the —CH$_2$— group attached to the 1' position of the aromatic ring. Number 2' represents the carbon atom of the aromatic ring below the 1' carbon atom, with numbers 2', C3'-C5' and 6' representing the other carbon atoms on the aromatic ring, going around the ring from number 1 towards number 6. For compound 7, numbers 1', 2', 3', 4', 5' and 6' represent the carbon atoms of the aromatic ring present in the methoxybenzoyl group, with the 1' carbon atom being attached to the carbonyl group and the 4' carbon atom being attached to the methoxy group, with numbers 2', 3', 5' and 6' representing the other carbon atoms on the aromatic ring, going around the ring from carbon atom number 1 towards carbon atom number 6.

TABLE 3

$^{13}$C Chemical Shifts (ppm) in CDCl$_3$

| Carbon no. | Compound |  |  |  |  |  |  |
|---|---|---|---|---|---|---|---|
|  | 1 | 2 | 3 | 4 | 5 | 6 | 7 |
| 1 | 139.0 | 138.0 | 138.7 | 138.5 | 138.7 | 138.5 | 137.8 |
| 2 | 113.4 | 113.5 | 113.2 | 113.4 | 113.2 | 113.3 | 113.5 |
| 3 | 160.1 | 160.1 | 160.0 | 160.0 | 159.9 | 159.9 | 159.9 |
| 4 | 113.4 | 113.2 | 113.1 | 113.2 | 113.1 | 113.0 | 113.4 |
| 5 | 129.7 | 130.0 | 129.9 | 130.0 | 129.8 | 129.9 | 129.9 |
| 6 | 119.7 | 119.8 | 119.7 | 119.7 | 119.7 | 119.7 | 120.1 |
| 7 | 48.4 | 48.6 | 48.4 | 48.6 | 48.5 | 48.4 | 49.7 |
| C=S | 182.8 | 181.5 | 181.6 | 181.4 | 182.1 | 181.8 | 180.2 |
| C=O |  |  |  |  |  |  | 166.3 |
| CH$_3$O | 55.2 | 55.3 | 55.2 |  | 55.3 | 55.2 | 55.6 |
| CH$_3$O' | 55.2 |  |  |  |  |  | 55.3 |
| 1' | 139.0 | 44.5 | 44.5 | 44.4 | 46.8 | 136.9 | 123.6 |
| 2' | 113.4 | 31.9 | 29.7 | 29.1 | 133.2 | 128.8 | 129.7 |
| 3' | 160.1 | 26.8 | 26.8 | 26.8 | 117.2 |  | 114.4 |
| 4' | 113.4 |  | 28.9 | 29.1 |  |  | 163.8 |
| 5' | 129.7 |  | 29.6 | 28.8 |  |  | 114.4 |
| 6' | 119.7 |  | 29.6 | 31.7 |  | 128.8 | 129.7 |
| 7' | 48.4 |  |  | 22.6 |  |  |  |
| 8' |  |  |  | 14.1 |  |  |  |
| C3'–C5' |  |  |  |  |  | 127.5–127.8 |  |
| C4'–C15' |  | 28.7–29.7 |  |  |  |  |  |
| C7'– |  |  | 29.3– |  |  |  |  |
| C9' |  |  | 29.5 |  |  |  |  |
| C10' |  |  | 31.9 |  |  |  |  |
| C11' |  |  | 22.7 |  |  |  |  |
| C12' |  |  | 14.1 |  |  |  |  |
| C16' |  | 31.9 |  |  |  |  |  |
| C17' | 22.7 |  |  |  |  |  |  |
| C18' | 14.1 |  |  |  |  |  |  |

An interesting feature about the above data included the clear difference in the carbonyl carbon resonance at 166.3 ppm and thiocarbonyl carbon at 182 ppm in the CMR spectra. Another unusual feature was the broad $^{13}$C resonance of the methylene in the 3-methoxybenzyl substituent that appeared in all of the compounds having that substitution.

TABLE 4

$^1$H Chemical Shifts (ppm) in CDCl$_3$

| Proton No. | Compound |  |  |  |  |  |  |
|---|---|---|---|---|---|---|---|
|  | 1 | 2 | 3 | 4 | 5 | 6 | 7 |
| H2 | 6.79 m | 6.89 m | 6.84 m | 6.88 m | 6.82 m | 6.77 m | 6.87 m |
| H4 | 6.79 m | 6.89 m | 6.84 m | 6.88 m | 6.82 m | 6.77 m | 6.98 m |

TABLE 4-continued $^1$H Chemical Shifts (ppm) in CDCl$_3$

| Proton No. | Compound | | | | | | |
|---|---|---|---|---|---|---|---|
| | 1 | 2 | 3 | 4 | 5 | 6 | 7 |
| H5 | 7.20 dd (8.0, 7.7) | 7.28 dd (7.9, 5.9) | 7.23 dd (7.9, 7.8) | 7.28 dd (7.3, 8.4) | 7.23 dd (7.8, 7.8) | 7.28 m | 7.29 dd (7.8, 4.0, 3.9) |
| H6 | 6.79 m | 6.89 m | 6.84 m | 6.88 m | 6.82 m | 6.77 m | 6.98 m |
| H7A,B | 4.54 bs | 4.65 bs | 4.58 bs | 4.63 bs | 4.61 bs | 4.58 bd | 4.80 d |
| 3-OCH$_3$ 4-OCH$_3$ | 3.74 s | 3.82 s | 3.77 s | 3.81 s | 3.77 s | 3.74 s | 3.81 s |
| H1' A,B | | 3.37 bs | 3.34 bs | 3.36 bs | 4.02 | 4.58 bd | |
| H2' | 6.79 m | | | | 5.79 ddt (17.2, 10.5, 5.5) | 7.28 m | 7.80 dd |
| H2' A,B | | 1.55 bs | 1.49 tt (6.5, 6.0) | 1.54 bs | | | |
| H3' | | | | | | 7.28 m | 6.98 m |
| H3' A,B | | | | | 5.14 m | | |
| (CH$_2$)$_n$ | | 1.27 m | 1.23 m | 1.25 m | | | |
| H4' | 6.79 m | | | | | | |
| H5' | 7.20 dd | | | | | 7.28 m | 6.98 m |
| H6' | 6.79 m | | | | | 7.28 m | 7.80 dd |
| 3-OCH$_3$' | 3.74 s | | | | | | |
| H7' A,B | 4.54 | | | | | | |
| Terminal CH$_3$ | | 0.89 t (6.7) | 0.87 t (6.7) | 0.89 t (6.7) | | | |

In Table 4, hydrogen atom numbers correspond to the carbon numbers to which they are bonded in the same compounds described above for Table 3. A,B3 refers to 2 hydrogen atoms bonded to the same carbon, m refers to multiplet, b refers to broad, t refers to triplet, d refers to doublet and s refers to singlet.

Molecular mechanics calculations were carried out using a modified version of the AMBER force field (Cornell W. D., Cieplak, P., Bayly, C. I., Gould, I. R., Merz, K. M., Jr., Ferguson, D. M., Spellmeyer, D. C., Fox, T., Caldwell, J. W. and Kollman, P. A., 1995, "A Second Generation Force Field for the Simulation of Proteins, Nucleic Acids and Organic Molecules," J. Am. Chem. Soc., 117, 5179–5197, and Momany, F. A., and Willett, J. L., 2000, "Computational Studies on Carbohydrates:In Vacuo Studies using a Revised AMBER Force Field, AMB99C, Designed for α-(1__>4) Linkages," Carbohydrate Res. 326, 194–209) as implemented in the MSI InsightII version 4.0/Discover programs (Molecular Simulations Inc., San Diego, Calif.). Atom typing and placing of atomic charges was carried out using the typing and charging algorithms in the MSI software. The dielectric constant was treated as $\epsilon=1$ with the electrostatic and nonbonded van der Waals 1–4 terms scaled by 0.5. Empirical energy minimizations were carried out to a gradient of less than ~0.001 kcal/mol. Explicit hydrogen atoms were included in all calculations, and hydrogen atoms were allowed to move on all molecules. Semiempirical AMI geometry optimization and frequency calculations were carried out using the AMPAC software installed in the MSI 4.0 Discover program.

Conformational analysis of 1,3-di(3-methoxybenzyl) thiourea was carried out by rotation about the 1–7, 3-O, N—C, and 7-N bonds of this compound. The torsional energy minima were treated as having 2-fold symmetry and thus two choices for each dihedral were taken as starting conform ations. Each conformer was energy minimized and the different conformations compared visually using MSI InsightII graphics software. The partial double bond character around the N—C bonds results in a planar N—(C=S)—N structure, and results in three possible stable conformations, trans-trans, trans-cis, and cis-cis. The cis-cis form of the compound was difficult to obtain with low energy, and was not considered further. However, it was possible to find low-energy conformer of the trans-cis, as well as the more extended trans-trans conformer. The low-energy conformers were studied by both empirical and semiempirical methods as a check of the geometry optimization. The resulting structures from both types of calculations are similar for each conformer, and the energy differences between conformers were also very close between the two computational methods.

The empirical energy calculation for 1,3-di(3-methoxybenzyl)thiourea gave a small energy preference to the trans-cis conformation, as a result of more close atom-atom interactions. The AMPAC AM1 results suggested that the conformers of the compound are identical in energy, with the compound having a large dipole moment. Although the trans-cis form of this compound is interesting because of the stacked aromatic rings, and would be stabilized in polar solvents, the vacuum free energy (AM1) favors, by over 6 kcal/mol, the extended trans-trans form over the trans-cis form. The extended forms are different in their three dimensional structures. For example, in the trans-trans form of 1,3-di(3-methoxybenzyl)thiourea, the C=S bond is at the apex of a pyramid shaped configuration, created by the spacer —CH$_2$— groups that allow the all trans configuration at the thiourea group. This exposure of the sulfur atom to reagents is also seen in the trans-cis form of this compound.

The NMR results were in agreement with the trans-trans conformations for 1,3-di(3-methoxybenzyl)thiourea being preferred in non-polar solvents, as all $^{13}$C chemical shifts were identical between the two sides of the molecule. One would expect that differences in the chemical shifts would be observed if the trans-cis conformations were populated in any significant amount. 1,3-di(3-methoxybenzyl)thiourea did not show ring current effects one would expect if the aromatic rings were stacked.

EXAMPLE 4

OSI Test of Jojoba Oil Mixed with 1,3-Di(3-Methoxybenzyl)Thiourea

Jojoba oil (extracted from jojoba seed with hexane) is a wax ester with monounsaturated C20 and C22 acids and alcohols esterified together. Jojoba oil (20 g) was mixed with 20 mg (0.1%) of the 1,3-di(3-methoxybenzyl)thiourea prepared in Example 3. An Oxidative Stability test at 110° C. on 5 g samples of the mixture (in triplicate) revealed an OSI time of 64.2 h, a 30% improvement compared to an OSI time of 49.2 h for the jojoba oil alone. OSI time is the time for oxygen bubbling through the oil at a constant rate to break the oil down and generate detectable oxidation products. When the 1,3-di(3-methoxybenzyl)thiourea product from Example 3 was added at the 1% level, OSI time increased to 168 h, a 241% improvement as compared to jojoba oil alone.

EXAMPLE 5

OSI Test of Unrefined (Crude) Meadowfoam Seed Oil Mixed with 1,3-Di(3-Methoxybenzyl)Thiourea Unrefined (crude) meadowfoam seed oil (20 g, Lot #C-9773, The Fanning Corp) was mixed with 20 mg (0.1%) of the 1,3-di(3-methoxybenzyl)thiourea prepared in Example 3. An Oxidative Stability test at 110° C. on 5 g samples of the mixture (in triplicate) revealed an OSI time of 76.4 h, a 15% improvement compared to an OSI time of 66.3 h for the meadowfoam oil alone. When the 1,3-di(3-methoxybenzyl)thiourea product from Example 3 was added at the 1% level, OSI time increased to 211 h, a 218% improvement.

EXAMPLE 6

OSI Test of Refined Meadowfoam Seed Oil Mixed with 1,3-Di(3-Methoxybenzyl)Thiourea The 1,3-di(3-methoxybenzyl)thiourea prepared in Example 3 was mixed at 0.1%, 0.5% or 1.0% with refined meadowfoam seed oil (Lot #CW-4551, The Fanning Corp) and the oxidative stability of the mixtures was compared to that of refined meadowfoam seed oil at 130° C. The OSI times were 49.8 h, 159 h and 172 h, respectively, for the mixtures containing the thiourea compared to an OSI time of 14.9 h for this lot of refined meadowfoam seed oil with no additives at 130° C. Accordingly, supplementing the refined meadowfoam seed oil with 0.1%, 0.5%, and 1.0% 1,3-di-3-methoxybenzyl thiourea provided increases in the OSI time of 234%, 967% and 1054%, respectively.

EXAMPLE 7

OSI Test of High Oleic Sunflower Oil Mixed with 1,3-Di(3-Methoxybenzyl)Thiourea High oleic sunflower oil is a highly monounsaturated vegetable oil. High oleic sunflower oil (20 g, Florasun Brand, Floratech, Gilbert, Ariz.) was mixed with 200 mg (1.0%) of the 1,3-di(3-methoxybenzyl)thiourea prepared in Example 3. An Oxidative Stability test at 130° C. on 5 g samples of the mixture (in triplicate) revealed an OSI time of 157 h, a 1720% improvement compared to an OSI time of 9.13 h for the sunflower oil alone.

EXAMPLE 8

OSI Test of Refined Meadowfoam Seed Oil Mixed with 1,3-Bis(2-Methoxyphenyl)-2-Thiourea Disubstituted thioureas available commercially that do not have a 3-methoxybenzyl moiety have lower antioxidant protection for monounsaturated oils. Thus, 1,3-bis(2-methoxyphenyl)-2-thiourea (Aldrich Chem Co.) added at 0.1% to refined meadowfoam oil gave an OSI time of 37.1 h at 130° C., a 34% lower value than for the 1,3-di-(3-methoxybenzyl) thiourea produced in Example 3. Likewise, 1,3-bis(3-methoxyphenyl)-2-thiourea at 0.1% added to refined meadowfoam oil gave an OSI time of 27.0 h, an 84% lower value than for the 1,3-di-(3-methoxybenzyl)thiourea produced in Example 3.

EXAMPLE 9

OSI Test of Soybean Oil Mixed with 1,3-Di(3-Methoxybenzyl)Thiourea

Soybean oil is a highly polyunsaturated vegetable oil. Soybean oil (20 g) was mixed with 200 mg (1.0%) of the 1,3-di(3-methoxybenzyl)thiourea prepared in Example 3. An Oxidative Stability test at 130° C. on 5 g samples of the mixture (in triplicate) revealed an OSI time of 6.4 h, an 831% improvement compared to an OSI time of 0.77 h for the soybean oil alone.

EXAMPLE 10

OSI Test of Milkweed Seed Oil Mixed with 1,3-Di (3-Methoxybenzyl)Thiourea

Milkweed seed oil is a highly polyunsaturated vegetable oil. Milkweed seed oil (20 g, extracted from the seed with hexane) was mixed with 200 mg (1.0%) of the 1,3-di(3-methoxybenzyl)thiourea prepared in Example 3. An Oxidative Stability test at 130° C. on 5 g samples of the mixture (in triplicate) revealed an OSI time of 2.78 h, an 654% improvement compared to an OSI time of 0.42 h for the milkweed oil alone.

EXAMPLE 11

Oxidative Stability by Rotating Pressure Vessel (RBOT) Tests of Mono- and Polyunsaturated Vegetable Oils Mixed with 3-Methoxybenzyl Thiourea Compounds In these experiments, Oxidative Stability by Rotating Pressure Vessel (RBOT) tests were performed with different 3-methoxybenzyl thiourea compounds synthesized in Example 3 that were mixed in different quantities with different mono- and polyunsaturated vegetable oils. Hexane was used to clean and store the copper coils, but all other aspects of the Oxidative Stability by Rotating Pressure Vessel (RBOT) test were the same as in the standard ASTM D2272-98 test method (ASTM, 2001, "Standard Test Method for Oxidation Stability of Steam Turbine Oils by Rotating Pressure Vessel," in Book of Standards, Vol. 05.01., American Society for Testing and Materials, West Conshohocken, Pa.). The results of these experiments are shown below in Table 5.

TABLE 5

Oxidative Stability by Rotating Pressure Vessel (RBOT) of Vegetable Oils with or without Added 3-Methoxybenzyl Thiourea Compounds

| Sample | Oxidative Stability (Minutes) |
|---|---|
| Crude Rapeseed Oil | 13 |
| Refined Rapeseed Oil | 15 |
| Refined Meadowfoam Seed Oil | 22 |
| Refined Meadowfoam Seed Oil Plus 0.05% 1,3-di(3-methoxybenzyl) thiourea | 33 |
| Refined Meadowfoam Seed Oil Plus 0.1% 1,3-di(3-methoxybenzyl) thiourea | 40 |
| Refined Meadowfoam Seed Oil Plus 0.2% 1,3-di(3-methoxybenzyl) thiourea | 41 |
| Refined Meadowfoam Seed Oil Plus 1.0% 1,3-di(3-methoxybenzyl) thiourea | 41 |
| Refined Meadowfoam Seed Oil Plus 0.1% 1-(3-methoxybenzyl)-3-octadecyl thiourea | 15 |
| Refined Meadowfoam Seed Oil Plus 0.1% 1-(3-methoxybenzyl)-3-dodecyl thiourea | 41 |
| Refined Meadowfoam Seed Oil Plus 0.1% 1-(3-methoxybenzyl)-3-octyl thiourea | 43 |
| Refined Meadowfoam Seed Oil Plus 0.1% 1-(3-methoxybenzyl)-3-(1-propenyl) thiourea | 24 |

TABLE 5-continued

Oxidative Stability by Rotating Pressure Vessel (RBOT) of
Vegetable Oils with or without Added 3-Methoxybenzyl Thiourea
Compounds

| Sample | Oxidative Stability (Minutes) |
|---|---|
| Refined Meadowfoam Seed Oil Plus 0.1% 1-(3-methoxybenzyl)-3-benzyl thiourea | 26 |
| Refined Meadowfoam Seed Oil Plus 0.1% 1-(3-methoxybenzyl)-3-(4-methoxybenzoyl) thiourea | 24 |

1,3-di(3-methoxybenzyl)thiourea was shown to be an effective antioxidant in these RBOT tests (as well as in the OSI tests described in the other examples) for mono- and polyunsaturated oils. Oxidative stability in the RBOT test doubled with the addition of 0.1% of 1,3-di(3-methoxybenzyl)thiourea, 0.1% 1-(3-methoxybenzyl)-3-dodecyl thiourea and 1-(3-methoxybenzyl)-3-octyl thiourea. Higher levels of 1,3-di(3-methoxybenzyl)thiourea did not increase the stability time. The addition of a carbonyl in 1-(3-methoxybenzyl)-3-(4-methoxybenzoyl)thiourea to increase UV absorbance lowered, but did not eliminate, the antioxidant capability of the thiourea.

EXAMPLE 12

Testing of Molar Absorpitivities of 3-Methoxybenzyl Thiourea Compounds

Chromophores that absorb strongly in the UVA and UVB ranges have found widespread use in sunscreens. Such chromophores as para-aminobenzoic acid (PABA) derivatives, cinnamates, and salicylate act to absorb incident photons before they interact with the skin. Further, overexposure to UVB light has been linked with production of skin cancers and suppression of the human imune system. UVB is the primary cause of delayed sunburn, occurring 12–24 hours after sun exposure. However, UVA may also be important in photoaging and skin cancers, and most sunscreens block UVB, but do not filter out the UVA frequencies.

The compounds synthesized in Example 3 were tested to determine their ability to absorb UVA and/or UVA light. UV spectra of quantitatively weighed and diluted samples (0.0 1 mg/ml) in chloroform were scanned from 244–450 nm at 240 nm/min on a Beckman DU 640 spectrophotometer (Beckman Coulter, Inc., Fullerton, Calif.). $A_{max}$ in the 280–320 nm range was determined and converted to molar absorptivity for the UVB region, and $A_{max}$ in the 320–400 nm range was determined and converted to molar absorptivity for the UVA region. The results of these experiments are set forth in Table 6 below.

TABLE 6

UVB (280–320 nm) and UVA (320–400 nm)
Molar Absorptivities of Compounds

| Compound | $UVB_{MAX}$ Molar Absorptivity | $UVA_{MAX}$ Molar Absorptivity |
|---|---|---|
| 1,3-di(3-methoxybenzyl) thiourea | 5367 | 0.0 |
| 1-(3-methoxybenzyl)-3-octadecyl thiourea | 850 | 0.0 |
| 1-(3-methoxybenzyl)-3-dodecyl thiourea | 2625 | 0.0 |

TABLE 6-continued

UVB (280–320 nm) and UVA (320–400 nm)
Molar Absorptivities of Compounds

| Compound | $UVB_{MAX}$ Molar Absorptivity | $UVA_{MAX}$ Molar Absorptivity |
|---|---|---|
| 1-(3-methoxybenzyl)-3-octyl thiourea | 2999 | 0.0 |
| 1-(3-methoxybenzyl)-3-(1-propenyl) thiourea | 2852 | 0.0 |
| 1-(3-methoxybenzyl)-3-benzyl thiourea | 2357 | 0.0 |
| 1-(3-methoxybenzyl)-3-(4-methoxybenzoyl) thiourea | 34090 | 1420 |
| trans-cinnamic acid | 22350 | 54 |

1,3-di(3-methoxybenzyl)thiourea was found to be one of the better UVB absorbers. Allyl and benzyl substitution did not improve UVB absorbance over the 1,3-di(3-methoxybenzyl)thiourea. However, replacement of one 3-methoxybenzyl substituent with 4-methoxybenzoyl substituent (1-(3-methoxybenzyl)-3-(4-methoxybenzoyl) thiourea) increased the UVA and UVB absorbance beyond that of trans-cinnamic acid, a common UV-absorbing substituent in sunscreens.

The large molar absorptivity found for 1-(3-methoxybenzyl)-3-(4-methoxybenzoyl)thiourea is due to the large electric dipole moment changes resulting from the electrons involved in transferring across relatively large regions of a conjugated complex. Molar absorptivity increases as the conjugated system becomes more extended, and this observation was consistent with the molecular differences between 1,3-di(3-methoxybenzyl)thiourea and 1-(3-methoxybenzyl)-3-(4-methoxybenzoyl)thiourea. 1,3-di (3-methoxybenzyl)thiourea showed typical aromatic molar absorptivity in the UVB range. The replacement of one 3-methoxybenzyl group in 1,3-di(3-methoxybenzyl) thiourea with 4-methoxybenzoyl in 1-(3-methoxybenzyl)-3-(4-methoxybenzoyl)thiourea expanded the conjugated system over a much larger space, and the result of adding this complex conjugated system is shown in Table 6 above as enhanced absorptivities in both the UVB and UVA frequency ranges.

EXAMPLE 13

Toxicity of 3-Methoxybenzyl Thiourea Compounds

An assay was performed to test the toxicity of the 3-methoxybenzyl thiourea compounds synthesized in Example 3. This assay was a modification of two previously published methods (Meyer, B. N., Ferrigni, N. R., Putnam, J. E., Jacobsen, L. B., Nichols, D. E. and McLaughlin, J. L., "Brine Shrimp: a Convenient General Bioassay for Active Plant Constituents," 1982, Planta Med. 45, 31–4, and Solis, P. N., Wright, C. W., Anderson, M. M., Gupta, M. P. and Phillipson, J. D., 1993, "A Microwell Cytotoxicity Assay using *Artemia salina* (Brine Shrimp)," Planta Med. 59, 250–2.).

Brine shrimp eggs (*Artemia salina*) were obtained from Brine Shrimp Direct, Ogden, Utah and stored at 10° C. until used. Eggs (400 mg) were added to 1 l of deionized water containing 40 g of sea salts (Sigma Chemical Co., St. Louis, Mo.). Air was bubbled through the resulting solution for 36 h at 27° C., at which time the naupli (first instar larva stage of the shrimp) were collected with a Pasteur pipette by attracting the organisms to one side of the vessel with a light source.

Test compounds (1–2 mg) were originally made up at a concentration of 1 mg/ml in artificial seawater, except for water insoluble compounds, which were dissolved in 50 μl of dimethyl sulfoxide (DMSO) prior to adding enough water to make a 1 mg/ml solution. Serial dilutions were performed in 100 μl of seawater in triplicate in the wells of a 96-well microplate to give appropriate concentrations. Control wells for both water and DMSO were included with each experiment. A 100 μl solution of naupli (10–30) was added to each well, and the covered plate was incubated for 24 h at 27° C. The number of non-motile, and the total number of, naupli were counted in each well using a binocular microscope (10×). $LC_{50}$ values were then calculated by Probit analysis (Finney, D. J., 1971, "Probit Analysis," 3rd Ed.; University Press: Cambridge [Eng.]). 1,3-di(3-methoxybenzyl) thiourea, 1-(3-methoxybenzyl)-3-octadecyl thiourea, 1-(3-methoxybenzyl)-3-dodecyl thiourea and 1-(3-methoxybenzyl)-3-octyl thiourea were precipitated out of solution upon the addition of water. The results of the toxicity assay are shown in Table 7 below.

TABLE 7

Activity of Antioxidants and 3-Methoxybenzyl Thiourea Compounds against Brine Shrimp (*Artemia Sauna*)

| Compound | $LC_{50}$ (μg/ml) |
| --- | --- |
| cycloheximide | 105 |
| 1,3-di(3-methoxybenzyl) thiourea | >1000 |
| 1-(3-methoxybenzyl)-3-octadecyl thiourea | 62.5 |
| 1-(3-methoxybenzyl)-3-dodecyl thiourea | 3.80 |
| 1-(3-methoxybenzyl)-3-octyl thiourea | 240 |
| 1-(3-methoxybenzyl)-3-(1-propenyl) thiourea | 232 |
| 1-(3-methoxybenzyl)-3-benzyl thiourea | 31.6 |
| 1-(3-methoxybenzyl)-3-(4-methoxybenzoyl) thiourea | 58.0 |
| D-α-tocopherol | >1000 |
| ascorbic acid | 315 |
| trans-cinnamic acid | 315 |
| butylated hydroxy aniline (BHA) | 12.2 |
| butylated hydroxy toluene (BHT) | 104 |

As Table 7 shows, toxicity of 1,3-di(3-methoxybenzyl) thiourea against cell division in brine shrimp was very low compared to four other common antioxidants, except D-α-tocopherol, which was comparable. 1-(3-methoxybenzyl)-3-(1-propenyl)thiourea and 1-(3-methoxybenzyl)-3-octyl thiourea also proved to have low toxicity in this test. The toxicity of 1-(3-methoxybenzyl)-3-dodecyl thiourea was high enough to consider its use in therapeutic tests for killing cancer cells.

EXAMPLE 14

Thermal Properties and Solubility of 3-Methoxybenzyl Thiourea Compounds in Refined Meadowfoam Seed Oil In order to determine the solubility of the 3-methoxybenzyl thiourea compounds synthesized in Example 3 in refined meadowfoam seed oil, calibration curves of thiourea concentration versus peak area were determined for a concentration range of 0.005 to 0.25 mg/ml in $CHCl_3$ on the HPLC system described hereinabove using the UV detector response at 218 nm. Typical retention times were 7–9 min for the thioureas. Samples were weighed accurately (about 0.1 g) into 1.00 g of refined meadowfoam seed oil and heated to temperature (either 30° C. or 50° C.) for 4 h with occasional shaking. The samples were cooled to room temperature overnight, centrifuged and 0.3 g of the supernatant oil was removed and diluted with 1 ml $CHCl_3$ for testing. The results of the solubility tests are set forth in Table 8 below.

TABLE 8

Solubility of 3-Methoxybenzyl Thiourea Compounds in Refined Meadowfoam Seed Oil

| Compound | Solubility at 30° C. (mg/ml) | Solubility at 50° C. (mg/ml) |
| --- | --- | --- |
| 1,3-di(3-methoxybenzyl) thiourea | 2481 | 3517 |
| 1-(3-methoxybenzyl)-3-octadecyl thiourea | 280 | 147 |
| 1-(3-methoxybenzyl)-3-dodecyl thiourea | 1043 | 909 |
| 1-(3-methoxybenzyl)-3-octyl thiourea | 3069 | 2488 |
| 1-(3-methoxybenzyl)-3-(1-propenyl) thiourea | 1671 | 981 |
| 1-(3-methoxybenzyl)-3-benzyl thiourea | 1051 | 1038 |
| 1-(3-methoxybenzyl)-3-(4-methoxybenzoyl) thiourea | 2760 | 1927 |

A dual cell Perkin Elmer differential scanning calorimeter (PE DSC 7, Norwalk, Conn.) was used to determine the thermal transitions of the compounds. All scans were carried out from 30° C. to 200° C. at a heating and cooling rate of 10° C. minute and 40° C./min, respectively, except for 1-(3-methoxybenzyl)-3-(1-propenyl)thiourea, for which the scans were carried out from 0° C. to 200° C. at a heating rate of 10° C./min, and 1-(3-methoxybenzyl)-3-octadecyl thiourea, for which both the heating and cooling rates were 10° C./min. 1,3-di(3-methoxybenzyl)thiourea and 1-(3-methoxybenzyl)-3-dodecyl thiourea were heated to 300° C., and 1-(3-methoxybenzyl)-3-(4-methoxybenzoyl)thiourea was heated to 250° C. to determine the decomposition temperature. The decomposition temperature was taken as the onset of a decrease in the slope of the temperature-heat flow DSC curve. The first heating curve was recorded in all cases, and liquid nitrogen was used to quench the samples after the first heating. The results of these experiments are set forth in Table 9 below.

TABLE 9

Thermal Properties of 3-Methoxybenzyl Thiourea Compounds

| Compound | Melting Peak, ° C. | Enthalpy of Melting, J/g | Decomposition Temperature |
| --- | --- | --- | --- |
| 1,3-di(3-methoxybenzyl) thiourea | 81.5 | 105 | 265 |
| 1-(3-methoxybenzyl)-3-octadecyl thiourea | 102* | 143 | >200 |
| 1-(3-methoxybenzyl)-3-dodecyl thiourea | 88.5 | 145 | 273 |
| 1-(3-methoxybenzyl)-3-octyl thiourea | 77.5 | 123 | >200 |
| 1-(3-methoxybenzyl)-3-(1-propenyl) thiourea | 39.8 | 65.3 | >200 |

TABLE 9-continued

Thermal Properties of 3-Methoxybenzyl Thiourea Compounds

| Compound | Melting Peak, °C. | Enthalpy of Melting, J/g | Decomposition Temperature |
|---|---|---|---|
| 1-(3-methoxybenzyl)-3-benzyl thiourea | 71.8 | 73.4 | >200 |
| 1-(3-methoxybenzyl)-3-(4-methoxybenzoyl) thiourea | 116 | 93.9 | >200 |

*A second, relatively small, melting peak occurred at 83.2° C.

As chain length increased from C8 to C12 to C18, the aliphatic substitution reduced the lipid solubility in meadowfoam seed oil. Heating the meadowfoam seed oil and antioxidant to 50° C., and then cooling to room temperature, allowed 1,3-di(3-methoxybenzyl)thiourea to surpass the octyl substituted thiourea in solubility. This was somewhat surprising, and demonstrated that 3-methoxybenzyl substitution had a significant effect on lipid solubility. Solubility depends on the energy to replace solute-solute bonding in crystals with solute-oil bonds in solution. 1-(3-methoxybenzyl)-3-(4-methoxybenzoyl)thiourea, which has both a carbonyl and thiocarbonyl group, melted somewhat higher than the other compounds, but had a comparable lipid solubility, apparently due to the 3-methoxybenzyl moiety. Allyl substitution resulted in a significantly lower melting point, and 1-(3-methoxybenzyl)-3-(1-propenyl)thiourea was somewhat more difficult to crystallize in the recovery from the reaction.

The examples set forth hereinabove show that 1,3-di(3-methoxybenzyl)thiourea, in particular, was an effective antioxidant in two different oxidative stability tests for mono- and polyunsaturated oils at the 0.1% level. It was also a stronger UVB absorber than most of the other disubstituted thioureas tested. Molecular models and calculations explained some of these results. The toxicity of 1,3-di(3-methoxybenzyl)thiourea was also very low compared to other thioureas, and to some commonly-used lipid antioxidants. Solubility in meadowfoam seed oil was highest for 1,3-di(3-methoxybenzyl)thiourea, among those tested at 50° C. Thus, 1,3-di(3-methoxybenzyl)thiourea (from meadowfoam oil, meadowfoam by-products, or synthesized) appears to meet many of the criteria for an effective lipid antioxidant.

While the present invention has been described herein with some specificity, and with reference to certain preferred embodiments thereof, those of ordinary skill in the art will recognize numerous variations, modifications and substitutions of that which has been described which can be made, and which are within the scope and spirit of the invention. It is intended that all of these modifications and variations be within the scope of the present invention as described and claimed herein, and that the invention be limited only by the scope of the claims which follow, and that such claims be interpreted as broadly as is reasonable.

Throughout this application, various books, patents and other publications have been cited. The entireties of each of these books, patents and publications are hereby incorporated by reference herein.

We claim:

1. A compound of the formula:

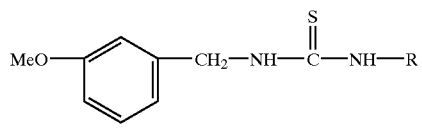

wherein R is a $C_1$–$C_{20}$ linear or branched alkenyl.

2. A compound of the formula:

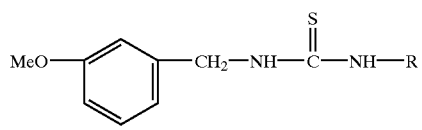

wherein R is a $C_5$–$C_7$ cycloalkenyl.

3. A compound of the formula:

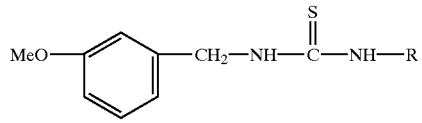

wherein R is benzoyl, a hydroxy-substituted benzoyl or an alkoxy-substituted benzoyl.

4. A compound of claim 1 wherein R is propenyl, butenyl, pentenyl, hexenyl, octenyl, decenyl, dodecenyl or octadecenyl.

5. A compound of claim 2 wherein R is cyclopentenyl, cyclohexenyl or cycloheptenyl.

6. A compound of claim 3 wherein R is benzoyl, hydroxybenzoyl, methoxybenzoyl or ethoxybenzoyl.

7. A compound of the formula:

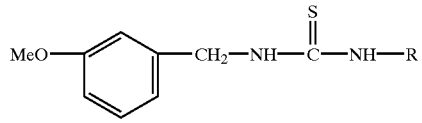

wherein R is a $C_1$–$C_{20}$ linear or branched alkyl, and wherein the compound is 1-(3-methoxybenzyl)-3-octadecyl thiourea.

8. A compound of the formula:
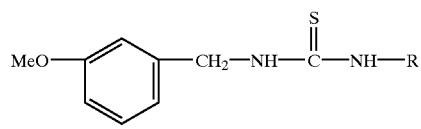
wherein R is a $C_1$–$C_{20}$ linear or branched alkyl, and wherein the compound is 1-(3-methoxybenzyl)-3-octyl thiourea.
9. A compound of claim 1 wherein the compound is 1-(3-methoxybenzyl)-3-(1-propenyl)thiourea.
10. A compound of claim 3 wherein the compound is 1-(3-methoxybenzyl)-3-(4-methoxybenzoyl)thiourea.
* * * * *

UNITED STATES PATENT AND TRADEMARK OFFICE
CERTIFICATE OF CORRECTION

PATENT NO. : 6,586,628 B2
DATED : July 1, 2003
INVENTOR(S) : Thomas P. Abbott and Alan Wohlman It is certified that error appears in the above-identified patent and that said Letters Patent is hereby corrected as shown below:

Column 17,
Line 49, cahnge "5'6'," to -- 5', 6', --.

Column 19,
Line 42, change "A,B3" to -- A,B --.

Signed and Sealed this

Twenty-first Day of June, 2005

JON W. DUDAS
*Director of the United States Patent and Trademark Office*